United States Patent
Choi et al.

(10) Patent No.: US 12,133,879 B2
(45) Date of Patent: Nov. 5, 2024

(54) EXOSOMES FOR TARGET SPECIFIC DELIVERY AND METHODS FOR PREPARING AND DELIVERING THE SAME

(71) Applicants: ILIAS BIOLOGICS INC., Daejeon (KR); ILIAS THERAPEUTICS, INC., New York, NY (US)

(72) Inventors: Chulhee Choi, Daejeon (KR); Nambin Yim, Daejeon (KR); Hojun Choi, Daejeon (KR); Kyungsun Choi, Daejeon (KR); Seung-Wook Ryu, Daejeon (KR)

(73) Assignees: ILIAS BIOLOGICS INC., Daejeon (KR); ILIAS THERAPEUTICS, INC., New York, NY (US)

( * ) Notice: Subject to any disclaimer, the term of this patent is extended or adjusted under 35 U.S.C. 154(b) by 0 days.

(21) Appl. No.: 18/412,403

(22) Filed: Jan. 12, 2024

(65) Prior Publication Data

US 2024/0207360 A1 Jun. 27, 2024

Related U.S. Application Data

(63) Continuation-in-part of application No. 16/887,029, filed on May 29, 2020, now Pat. No. 11,872,193, and a continuation-in-part of application No. 16/639,740, filed as application No. PCT/IB2018/056200 on Aug. 16, 2018, now abandoned, said application No. 16/887,029 is a continuation of application No. 15/803,338, filed on Nov. 3, 2017, which is a continuation-in-part of application No. PCT/KR2017/011070, filed on Sep. 30, 2017, said application No. PCT/IB2018/056200 is a continuation-in-part of application No. PCT/KR2016/004750, filed on May 4, 2016.

(60) Provisional application No. 62/659,816, filed on Apr. 19, 2018.

(30) Foreign Application Priority Data

| May 4, 2015 | (KR) | 10-2015-0062604 |
| Aug. 27, 2015 | (KR) | 10-2015-0120934 |
| Sep. 30, 2016 | (KR) | 10-2016-0126335 |
| Sep. 30, 2016 | (KR) | 10-2016-0126921 |
| Sep. 30, 2016 | (KR) | 10-2016-0126961 |
| Oct. 4, 2016 | (KR) | 10-2016-0127486 |
| Oct. 13, 2016 | (KR) | 10-2016-0132616 |
| Feb. 10, 2017 | (KR) | 10-2017-0018637 |
| Aug. 17, 2017 | (KR) | 10-2017-0104171 |

(51) Int. Cl.
| A61K 47/69 | (2017.01) |
| A61K 38/17 | (2006.01) |
| C07K 14/705 | (2006.01) |
| C07K 16/18 | (2006.01) |
| C07K 16/28 | (2006.01) |
| C12N 15/62 | (2006.01) |
| C12N 15/85 | (2006.01) |
| C12P 21/02 | (2006.01) |
| A61K 38/00 | (2006.01) |

(52) U.S. Cl.
CPC ........ *A61K 38/177* (2013.01); *A61K 47/6917* (2017.08); *C07K 14/705* (2013.01); *C07K 14/70596* (2013.01); *C07K 16/18* (2013.01); *C07K 16/28* (2013.01); *C12N 15/62* (2013.01); *C12N 15/85* (2013.01); *C12P 21/02* (2013.01); *A61K 38/00* (2013.01); *C07K 2317/80* (2013.01); *C07K 2319/03* (2013.01); *C07K 2319/70* (2013.01)

(58) Field of Classification Search
None
See application file for complete search history.

(56) References Cited

U.S. PATENT DOCUMENTS

| 2004/0136985 A1 | 7/2004 | Jennings et al. |
| 2016/0137716 A1 | 5/2016 | El Andaloussi et al. |

FOREIGN PATENT DOCUMENTS

| KR | 10-2016-0130937 A | 11/2016 |
| KR | 10-2016-0130949 A | 11/2016 |
| WO | 2010/119256 A1 | 10/2010 |
| WO | 2013/084001 A1 | 6/2013 |
| WO | 2014/168548 A2 | 10/2014 |
| WO | 2015/002956 A1 | 1/2015 |

OTHER PUBLICATIONS

Chen et al., ACS Appl Mater Interfaces Feb. 22, 2017;9(7):5864-5873 (Year: 2017).*
Sanchez-Navarro et al., Acc Chem Res. Aug. 15, 2017;50(8):1847-1854 (Year: 2017).*
Liu et al. Biomaterials. Jul. 2010;31(19):5246-57 (Year: 2010).*

(Continued)

*Primary Examiner* — Daniel C Gamett
(74) *Attorney, Agent, or Firm* — Morgan, Lewis & Bockius LLP

(57) ABSTRACT

The present invention provides a method for producing an exosome that transfers an active substance specifically to a target and the exosome produced by the same; a method for delivering the active substance to the target tissue using the exosome; a pharmaceutical composition for delivery of the active substance comprising the exosome as an active ingredient; and a composition for preparing the exosome comprising an expression vector wherein the target peptide is inserted into an extracellular portion of a transmembrane protein.

16 Claims, 6 Drawing Sheets

Specification includes a Sequence Listing.

(56) References Cited

OTHER PUBLICATIONS

Wei et al., Angew Chem Int Ed Engl. Mar. 2, 2015;54(10):3023-3027 (Year: 2015).*
Badr-Eldin et al.. Int J Mol Sci. Aug. 21, 2022;23(16):9440 (Year: 2022).*
Oller-Salvia et al Angew Chem Int Ed Engl. Jan. 11, 2016;55(2):572-575 (Year: 2016).*
Reginald-Opara et al., Int J Pharm. Oct. 15, 2022;626:122152 (Year: 2022).*
Stojanov et al. Mol Pharm. Jun. 4, 2012;9(6):1620-1627 (Year: 2012).*
Vilella et al., J Control Release. Jan. 28, 2014;174:195-201 (Year: 2014).*
Guo et al., J Control Release. Apr. 10, 2020;320:347-362 (Year: 2020).*
Opačak-Bernardi et al., J Drug Target. Jul. 2017;25(6):523-531 (Year: 2017).*
Zhang et al. Biomaterals vol. 34, Issue 36, Dec. 2013, pp. 9171-9182 (Year: 2013).*
Ni et al., J Neurooncol. Jun. 2020;148(2):245-258 (Year: 2020).*
International Search Report issued Apr. 25, 2019 for International Patent Application No. PCT/IB2018/56200.
Office Action issued Aug. 10, 2022 for Indian Patent Application No. 202047010520 (Partial Translation).
Office Action issued Sep. 28, 2022 for U.S. Appl. No. 16/639,740.
Office Action issued Apr. 20, 2023 for U.S. Appl. No. 16/639,740.
Office Action issued Nov. 30, 2023 for U.S. Appl. No. 16/639,740.
Office Action issued Oct. 24, 2022 for Australian Patent Application No. 2021250906.
Sequence alignment, 2023, 1 page total.
Stickney, et al., "Development of exosome surface display technology in living human cells", 2016, Biochemical and Biophysical Research Communications, vol. 472, p. 54-59.
Zhang, et al. "Dual-functional nanoparticles targeting amyloid plaques in the brains of Alzheimer's disease mice", 2014, Biomaterials, vol. 35, p. 456-465.
Ohno, et al., "Systematically Injected Exosomes Target to EGFR Deliver Antitumor MicroRNA to Breast Cancer Cells", 2013, Molecular Therapy, vol. 21, p. 185-191.
Alvarez-Ervity, et al., "Delivery of siRNA to the mouse brain by systemic injection of target exosomes", 2011, Nature Biotechnology, vol. 29, Issue No. 4, p. 341-345.
Johnsen, et al., "A comprehensive overview of exosomes as drug delivery vehicles—Endogenous nanocarriers for targeted cancer therapy", 2014, Biochimica et Biophysica Acta, vol. 1846, p. 75-87.
Spencer, et al., "Peripheral Delivery of a CNS Targeted, Metalo-Protease Reduces Aβ Toxicity in a Mouse Model of Alzheimer's Disease", 2011, PLOS One, vol. 6, Issue No. 1, p. 1-12.
Ha, et al., "Exosomes as therapeutic drug carriers and delivery vehicles across biological membranes: current perspectives and future challenges", 2016, Acta Pharmaceutica Sinica B, vol. 6, Issue No. 4, p. 287-296.
Kotmakçi, et al., "Extracellular Veicles as Natural Nanosized Delivery Systems for Small-Molecule Drugs and Genetic Material: Steps toward the Future Nanomedicines", 2015, J. Pharm. Pharm. Sci., vol. 18, Issue No. 3, p. 396-413.

* cited by examiner

EXOSOMES FOR TARGET SPECIFIC DELIVERY AND METHODS FOR PREPARING AND DELIVERING THE SAME

CROSS REFERENCE TO RELATED APPLICATIONS

This application claims benefit from Korean Patent Application No. 10-2017-0104171 filed Aug. 17, 2017, and U.S. Provisional Application No. 62/659,816 filed Apr. 19, 2018, the contents of each of which are incorporated herein by reference.

SEQUENCE LISTING SUBMISSION VIA PATENT CENTER

A computer readable xml file, entitled "128742-5001-US-01_Sequence Listing_ST26.xml," created on or about Mar. 12, 2024, with a file size of 109,707 bytes contains the sequence listing for this application and is hereby incorporated by reference in its entirety.

FIELD OF THE INVENTION

The present invention relates to a method for preparing an exosome that delivers a substance in a target specific manner and an exosome prepared by the method.

BACKGROUND OF THE INVENTION

The human body is composed of about 200 kinds of 100 trillion cells, in which the physiological activity is regulated by the action of various proteins to maintain life.

Cells are surrounded by membranes in bilayer structure composed of phospholipids, which block the entry of foreign substances into cells. Most of the protein drugs which have developed so far cannot pass through the cell membrane to enter the cell and can act on the outside of the cell or act on a receptor on the cell membrane to deliver the signal into the cell in order to show physiological effect.

Cytosol has lots of proteins which interact with each other to regulate physiological activity. So, if only a protein drug can be delivered inside the cell, that is, inside the cytosol, the cell activity would be controlled more effectively.

Recently, studies have been actively going on to establish a method for delivering a target protein directly into cells via cell membrane. When a recombinant protein of a target protein and protein transduction domains (PTDs), the peptide that passes through the cell membrane, is prepared and administered, it can enter the cytosol through the cell membrane. PTD is exemplified by HIV-1 TAT, HSV VP22, Antp, dfTAT, and Hph-1. A fusion protein prepared by combining the PTDs and a target protein is produced as a recombinant protein and at this time a separation process is required. However, this process is problematic in that the protein refolding is not performed properly, the activity is decreased, the protein is nonspecifically transferred, the risk of causing an immune reaction in vivo is large, the cost is high, and the yield is low.

On the other hand, a target protein combined with various nanoparticles such as Gold NP (nano particle), Liposome NP, Magnetic NP, and Polymeric NP can enter the cytoplasm through the cell membrane by endocytosis. However, most of the complexes of nanoparticles and target proteins are degraded in lysosomes in cells. If the target protein is degraded inside the lysosome, the activity of the protein is lost. Furthermore, it is difficult to separate the target protein and the nanoparticles in the cytoplasm, and the toxicity of the nanoparticles may be a problem as well.

Exosome is a small vesicle with a membrane structure in the size of 50~200 nm, which is secreted out of the cell with containing protein, DNA, and RNA for intercellular signaling.

Exosome was first found in the process of leaving only hemoglobin in the red blood cells by eliminating intracellular proteins at the last stage of red cell maturation. From the observation under electron microscope, it was confirmed that exosome is not separated directly from plasma membrane but discharged extracellular from the intracellular specific zone, called multivesicular bodies (MVBs). That is, when MVBs are fused with plasma membrane, such vesicles are discharged outside of the cell, which are called exosome.

It has not been clearly disclosed the molecular mechanism of the exosome generation. However, it is known that various immune cells including B-lymphocytes, T-lymphocytes, dendritic cells, megakaryocytes, and macrophages, stem cells, and tumor cells produce and secrete exosomes when they are alive.

Exosome contains various intracellular proteins, DNA, and RNA. These substances contained in the exosome secreted out of the cell and can be reintroduced into other cells by fusion or endocytosis and serve as intercellular messengers.

Exosomes with the desired protein inside can be used to treat various diseases in vivo. This requires efficient production of exosomes containing target proteins. Korean Patent Registration No. 10-0519384 discloses a method comprising:

1) the introduction of a gene for a specific antigen into a cell line;
2) stable expression of the protein produced from the introduced gene in the cell line; and
3) releasing it out of the cell through the exosome, and a method of using the produced exosome as a vaccine.

However, since the exosome is formed naturally in cells, even when a gene encoding a target protein is introduced into the production cells, the possibility of preparing the exosome containing the target protein is very low. There is a problem that the delivery efficiency of the exosome to the target tissue is low.

The tetraspanin family has four transmembrane domains, intracellular N- and C-termini and two extracellular loops protrude between the first and second, and third and fourth transmembrane domains.

CD9 is a 24-27 kD sized cell surface glycoprotein receptor belonging to the tetraspanin family, which regulates signal transduction actions important for regulating cell development, activity, growth and motility. In addition, it can regulate cell adhesion and cell migration and induces platelet activation involved in platelet-induced endothelial cell proliferation. In addition, it promotes muscle cell fusion and contributes to the maintenance of root canal.

The present invention provides a method for producing an exosome for target specific delivery comprising: preparing an expression vector by inserting a target peptide into an extracellular membrane domain of a transmembrane protein of an exosome; and producing the exosome comprising the target peptide located at the exosome membrane. Further, the present invention shows that the inserted target peptide is well expressed in HEK293T cells and that an active substance trapped in the exosome is well transferred into a target tissue.

SUMMARY OF THE INVENTION

A certain embodiment of the present invention provides a method for producing the exosome that transfers the active substance specifically to the target tissue and the exosome produced by the same.

Another embodiment of the present invention provides a method for delivering the active substance to the target tissue using the exosome.

Still another embodiment of the present invention provides a pharmaceutical composition for the delivery of an active substance comprising the exosome as an active ingredient.

Still another embodiment of the present invention provides an expression vector wherein the target peptide is inserted into the extracellular membrane domain of the transmembrane protein.

BRIEF DESCRIPTION OF THE DRAWINGS

FIG. 1B is a brief diagram showing insertion location of the target peptide in the CD9 protein structure.

DETAILED DESCRIPTION OF THE INVENTION

Figure 1A:
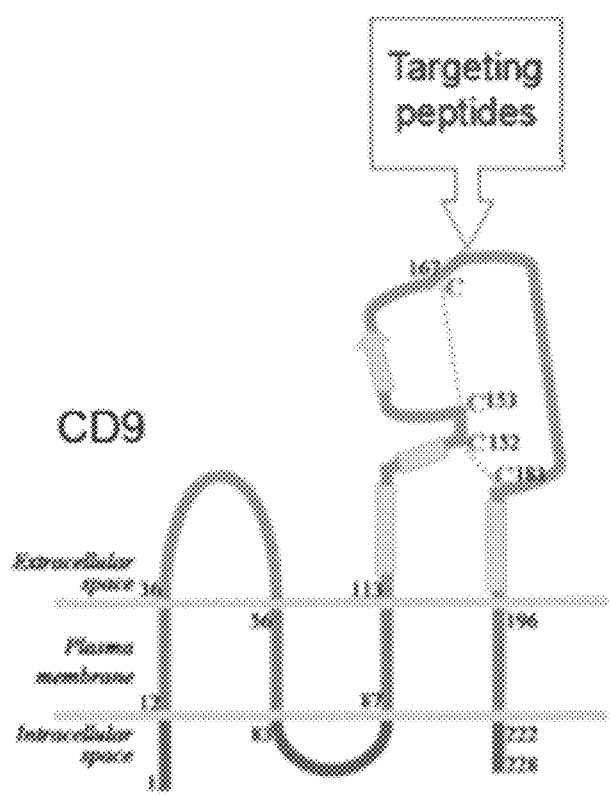
FIG. 1A is a schematic diagram of a pSF-CMV-CMV-Sbfl vector comprising a CIBN gene, an EGFP gene, and a target peptide inserted CD9 gene complex.

The present invention provides the method for producing the exosome that delivers the active substance specifically to the target tissue and the exosome produced by the same.

Another embodiment of the present invention provides the method for delivering the active substance to the target tissue using the exosome.

Still another embodiment of the present invention provides the pharmaceutical composition for the delivery of the active substance comprising the exosome as the active ingredient.

Still another embodiment of the present invention provides the expression vector wherein the target peptide is inserted into the extracellular membrane domain of the transmembrane protein.

The present invention relates to 1) the method for preparing the expression vector by inserting the target peptide into the extracellular membrane domain of the transmembrane protein of the exosome; and 2) the method for producing the exosome for target specific delivery of the active substance by introducing the said expression vector into an exosome-producing cell.

As used herein, the term "transmembrane protein" is a protein which locates and attached to the lipid bilayer of cells. It has hydrophobic regions containing a high fraction of polar amino acids. Certain hydrophobic regions locate inside the bilayer while more hydrophilic regions are in contact with the aqueous intracellular and extracellular environments. In one embodiment of the invention, the transmembrane protein is selected from the group such as, but not limited to tetraspanin, integrin, ICAM-1, MHC-I, MHC-II, annexin and Rab.

As used herein, the term "tetraspanin" is a membrane protein that has four transmembrane domains, presented on the cell membrane and receives information between cells and regulates cell proliferation. The tetraspanin is one or more proteins selected from the group comprising CD9, CD37, CD53, CD63, CD81 and CD82. In one embodiment of the invention, the tetraspanin is CD9.

The term "target peptide" as used herein, is a peptide capable of transferring a substance to a specific site in vivo. It is expressed on the surface of the exosome, allowing the exosome to migrate to the specific tissue. According to the present invention, any peptide able to migrate to the specific tissue can be used as the target peptide. In one embodiment of the invention, the target peptide is selected from but not limited to angiopeptin-2, ApoB, ApoE, VCAM-1 internalization sequence, striated muscle target peptide, Peptide-22, THR, THR retro-enantio, CTR, Leptin 20, RVG 29, CDX, Apamin, MiniAp-4, GSH, G23, g7, TGN, TAT(45-57), SynB1, Diketopeperazines and PhPro. The target peptide is inserted into the extracellular membrane domain of the transmembrane protein, wherein the insertion does not affect the expression or the function of the transmembrane. For example, the target peptide is inserted between amino acid position 170-171 from the N-terminus of the CD9 (SEQ ID NO: 3).

The term "specific site" as used herein, is the specific tissue where the target peptide migrates to. In one embodiment of the invention, the specific site is selected from but not limited to blood brain barrier, inflamed blood vessels, striated muscle, liver and cancer tissue.

The "expression vector" refers to a recombinant vector capable of expressing a desired peptide from a desired host cell, including an operatively linked necessary regulatory element to express the gene insert. The expression vector comprises expression control elements such as an initiation codon, a termination codon, a promoter, and an operator, etc. The initiation codon and the termination codon are generally considered as a nucleotide sequence and must be in frame with a coding sequence to encode a polypeptide. The promoter of the vector can be constitutive or inducible.

The term "operably linked" of the present invention means a functional linkage between a nucleic acid expression sequence and a nucleic acid sequence encoding a desired protein or RNA to perform a general function. For example, the expression of the coding sequence can be affected by operably linked a promoter and the protein or RNA coding nucleic sequence. The operable linkage with the expression vector can be produced by using recombinant DNA techniques well known in the art. A site-specific DNA cleavage and linkage can be achieved by using enzymes generally known in the art.

In addition, the expression vector may further includes a "selection marker". Selection markers are markers for selection of a transformed microorganism or a recombinant vector which is used to confer selectable phenotypes, such as drug resistance, nutritional requirements, resistance to cytotoxic agents or expression of surface proteins. The transformed cells are selected using the vector containing the selection marker, as only the cells expressing the selection marker in the selected agent's environment can survive. The selection marker is selected from but not limited to the antibiotic resistance gene, for example kanamycin, ampicillin, and puromycin.

The "exosome-producing cell" is one or more selected from the group consisting of B-lymphocytes, T-lymphocytes, dendritic cells, macrophage cells, macrophages, stem cells, and tumor cells. In one embodiment of the invention, the exosome-producing cell is HEK293T cell.

As used herein, the term "active substance" refers to a substance that enhances or inhibits a biological function, wherein the active substance controls the secretion of substances that regulate the function of the human body exhibiting abnormal conditions. The active substance is selected from but not limited to a protein drug, an enzyme, a nucleic acid, a chemical and a mixture thereof.

Figure 2:
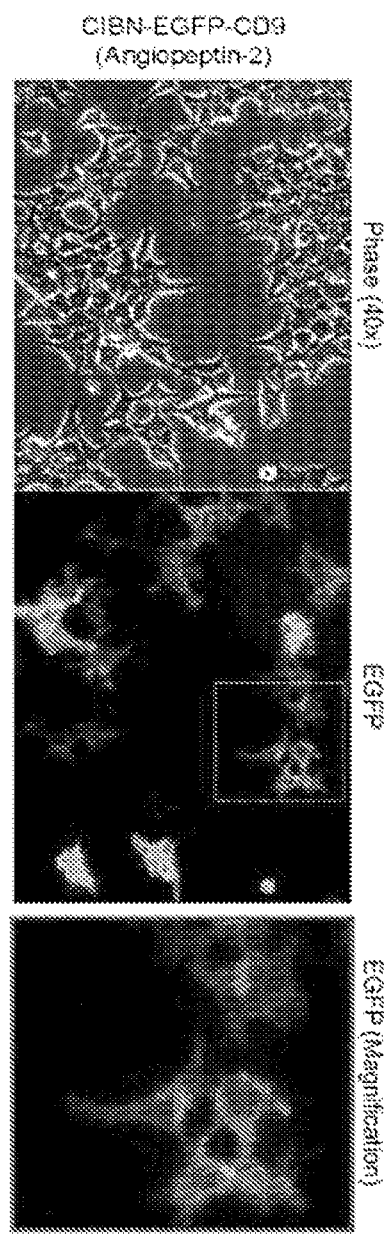
FIG. 2 is an image showing the expression of an Angiopeptin-2 peptide complex in HEK293T cells treated with the exosome comprising the Angiopeptin-2 peptide complex.
Figure 5:
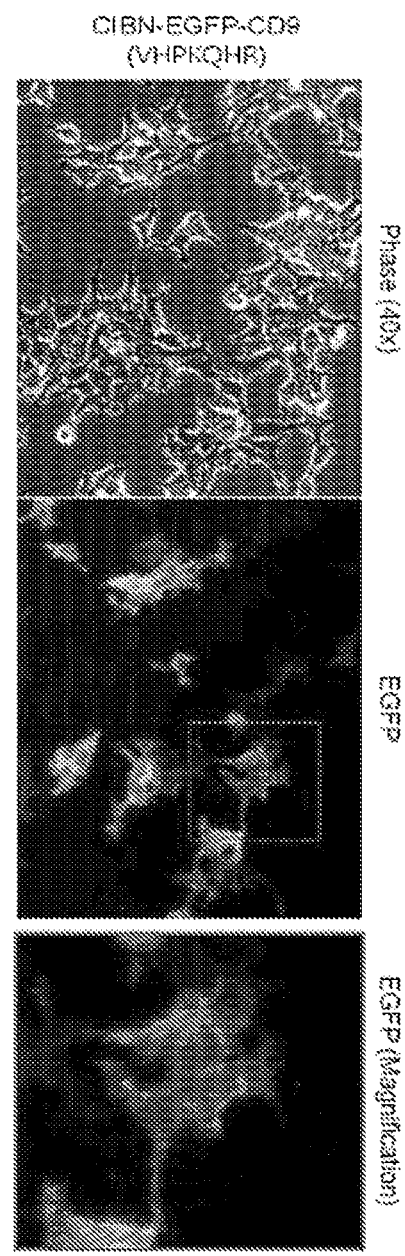
FIG. 5 is an image showing the expression of a VCAM-1 internalization sequence peptide complex in HEK293T cells treated with the exosome comprising the VCAM-1 internalization sequence peptide complex.
Figure 6:
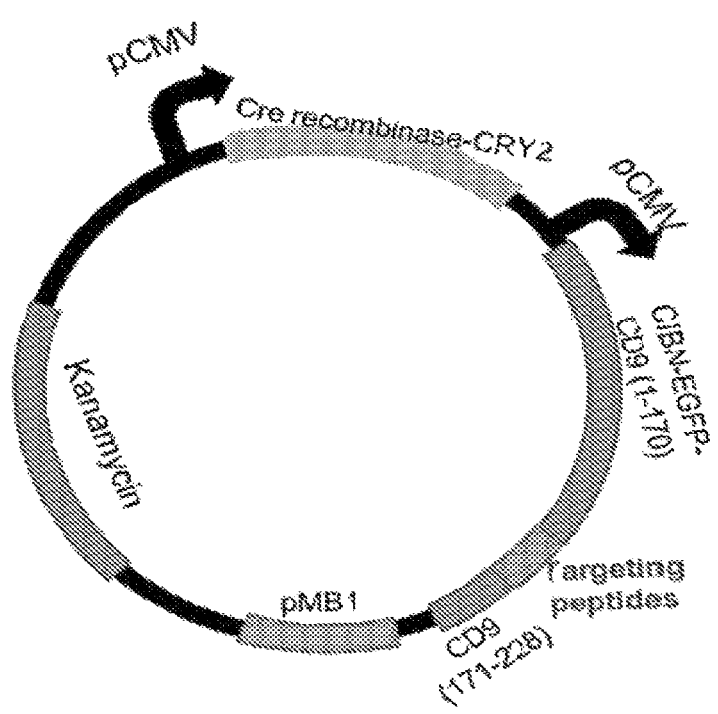
FIG. 6 shows a schematic diagram of a pSF-CMV-CMV-Sbfl vector comprising a Cre recombinase-CRY2 gene, the CIBN gene, the EGFP gene, and the target peptide inserted CD9 gene complex.

One embodiment of the present invention provides the pSF-CMV-CMV-Sbfl vector comprising the CIBN gene, the EGFP gene, and the target peptide complex inserted CD9 encoding gene, wherein the target peptide is selected from but not limited to angiopeptin-2, ApoB, ApoE, VCAM-1 internalization sequence, striated muscle target peptide, Peptide-22, THR, THR retro-enantio, CTR, Leptin 20, RVG 29, CDX, Apamin, MiniAp-4, GSH, G23, g7, TGN, TAT(45-57), SynB1, Diketopeperazines and PhPro. The said vector is introduced into exosome-producing cells such as HEK293T cells to obtain exosomes with target peptide labeled in the membrane protein (FIG. 1). FIGS. 2 and 5 show the expression of the target peptide in exosome membrane protein.

The present invention also provides the method for producing the exosome for target specific delivery of the active substance comprising:
1) preparing the expression vector by inserting the target peptide into the extracellular membrane domain of the transmembrane protein; and
2) introducing the expression vector of step 1) into the exosome-producing cell.

The transmembrane protein is selected from the group such as, but not limited to tetraspanin, integrin, ICAM-1, MHC-I, MHC-II, annexin and Rab. The tetraspanin is selected from the group consisting CD9, CD37, CD53, CD63, CD81 and CD82. In one embodiment of the invention, the tetraspanin is CD9.

The target peptide is any peptides able to migrate to the specific tissue. In one embodiment of the invention, the target peptide is selected from but not limited to angiopeptin-2, ApoB, ApoE, VCAM-1 internalization sequence, striated muscle target peptide, Peptide-22, THR, THR retro-enantio, CTR, Leptin 20, RVG 29, CDX, Apamin, MiniAp-4, GSH, G23, g7, TGN, TAT (45-57), SynB1, Diketopeperazines and PhPro.

The exosome-producing cell is one or more selected from the group comprising B-lymphocytes, T-lymphocytes, dendritic cells, macrophage cells, macrophages, stem cells, or tumor cells. In one embodiment of the invention, the exosome-producing cell is HEK293T cell.

In a specific embodiment of the present invention provides the pSF-CMV-CMV-Sbfl vector comprising the CIBN gene, the EGFP gene, and the target peptide complex inserted CD9 encoding gene, wherein the target peptide is selected from but not limited to angiopeptin-2, ApoB, ApoE, VCAM-1 internalization sequence and striated muscle target peptide. The said vector is introduced into exosome-producing cells such as HEK293T cells to obtain exosomes with target peptide labeled in the membrane protein (FIG. 1B). FIGS. 2 and 5 shows the expression of the target peptide in exosome membrane protein.

The present invention also provides the method for delivering the active substance to the target tissue using the exosome prepared by the method of the present invention.

The method comprises:
1) preparing the expression vector by inserting the target peptide into the extracellular membrane domain of the transmembrane protein; and
2) introducing the expression vector of step 1) into the exosome-producing cell.

The transmembrane protein is selected from the group such as, but not limited to tetraspanin, integrin, ICAM-1, MHC-I, MHC-II, annexin and Rab. The tetraspanin is selected from the group consisting CD9, CD37, CD53, CD63, CD81 and CD82. In one embodiment of the invention, the tetraspanin is CD9.

The target peptide is any peptides able to migrate to the specific tissue. In one embodiment of the invention, the target peptide is selected from but not limited to angiopeptin-2, ApoB, ApoE, VCAM-1 internalization sequence, striated muscle target peptide, Peptide-22, THR, THR retro-enantio, CTR, Leptin 20, RVG 29, CDX, Apamin, MiniAp-4, GSH, G23, g7, TGN, TAT (45-57), SynB1, Diketopeperazines and PhPro.

The exosome-producing cell is one or more selected from the group comprising B-lymphocytes, T-lymphocytes, dendritic cells, macrophage cells, macrophages, stem cells, or tumor cells. In one embodiment of the invention, the exosome-producing cell is HEK293T cell.

In a specific embodiment of the present invention provides the pSF-CMV-CMV-Sbfl vector comprising the CIBN gene, the EGFP gene, and the target peptide complex inserted CD9 encoding gene, wherein the target peptide is selected from but not limited to angiopeptin-2, ApoB, ApoE, VCAM-1 internalization sequence and striated muscle target peptide. The said vector is introduced into exosome-producing cells such as HEK293T cells to obtain exosomes with target peptide labeled in the membrane protein (FIG. 1B). FIGS. 2 and 5 shows the expression of the target peptide in exosome membrane protein.

The present invention also provides the pharmaceutical composition for the delivery of the active substance comprising the exosome as the active ingredient, wherein the amount of the exosome is about 10 to about 95% of the total weight of the composition.

The pharmaceutical composition of the present invention further comprises one or more active ingredients showing the same or similar functions to the above-mentioned active ingredient.

The pharmaceutical composition of the present invention further comprises pharmaceutically acceptable carriers, diluents, excipients and a mixture thereof. The pharmaceutically acceptable carrier is selected from but not limited to, chemicals listed in Merck Index, 13th ed., Merck & Co. Inc., saline solution, sterilized water, Ringer's solution, buffered saline, dextrose solution, maltodextrin solution, glycerol, ethanol and a mixture thereof. The pharmaceutical composition further comprises other conventional additives such as an antioxidant, a buffer, and a bacteriostatic agent.

The pharmaceutical composition further comprises a diluent or an excipient such as a filler, an extender, a binder, a wetting agent, a disintegrating agent, and a surfactant.

The pharmaceutical composition of the present invention is formulated into an oral or a parenteral preparation.

A solid formulation for the oral administration includes tablets, pills, powders, granules, capsules, troches and thereof. The solid formulation for the oral administration comprises one or more excipients such as starch, calcium carbonate, sucrose, lactose, gelatin, and thereof. The solid formulation further comprises lubricants such as magnesium stearate and talc.

A liquid formulation for the oral administration includes suspensions, solutions, emulsions, syrups and thereof. The liquid formulation comprises wetting agents, sweeteners, fragrances, preservatives and thereof.

The parenteral administration includes injections such as sterile aqueous solutions, non-aqueous solutions, suspensions, and emulsions. The non-aqueous solvent and the suspending agent is selected from the group comprising propylene glycol, polyethylene glycol, vegetable oil such as olive oil, injectable ester such as ethyl oleate, or thereof.

The pharmaceutical composition of the present invention is administered orally or parenterally according to the desired method. The parenteral administration is selected from external and intraperitoneal injection, intraperitoneal injection is selected from but not limited to rectal injection, subcutaneous injection, intravenous injection, and intramuscular injection.

The pharmaceutical composition according to the invention is administered in a pharmaceutically effective amount. The pharmaceutical effective amount varies on the type of disease, severity, activity of the drug, sensitivity to the drug, administration time, administration route, rate of excretion, duration of treatment, concurrent medication and thereof. The pharmaceutical composition of the present invention is administered alone or in combination with other therapeutic agents. When co-administered with other therapeutic agents, administration may be sequential or simultaneous.

The pharmaceutical composition of the present invention comprises the active ingredient wherein the pharmaceutically effective amount is 0.001-10 g/Kg, 0.01-8 g/Kg or 0.1-5 g/Kg. The administration can be once or several times a day.

In addition, the present invention provides the expression vector wherein the target peptide is inserted into the extracellular domain of the transmembrane protein.

The transmembrane protein is selected from the group such as, but not limited to tetraspanin, integrin, ICAM-1, MHC-I, MHC-II, annexin and Rab. The tetraspanin is one or more proteins selected from the group comprising CD9, CD37, CD53, CD63, CD81 or CD82. In one embodiment of the invention, the tetraspanin is CD9.

The target peptide is selected from but not limited to angiopeptin-2, ApoB, ApoE, VCAM-1 internalization sequence, striated muscle target peptide, Peptide-22, THR, THR retro-enantio, CTR, Leptin 20, RVG 29, CDX, Apamin, MiniAp-4, GSH, G23, g7, TGN, TAT(45-57), SynB1, Diketopeperazines and PhPro.

The expression vector is the recombinant vector capable of expressing the peptide of interest from the desired host cell, including the operatively linked necessary regulatory element to express the gene insert. The expression cells further comprise the selection marker. The selection marker is selected from but not limited to the antibiotic resistance gene, such as kanamycin, ampicillin, or puromycin. Any selection marker known in the art can be used.

The pharmaceutical composition may further comprises one or more other component compositions, solutions or devices suitable for the introduction of the expression vector, the culturing the transformed exosome producing cell, or the isolation and purification of the exosome produced from the transformed cells. For example, the composition further comprises a buffer suitable for the introduction of the expression vector, a medium and a container necessary for the culturing the transformed exosome producing cell and thereof.

An embodiment of the present invention provides the pSF-CMV-CMV-Sbfl vector comprising the CIBN gene, the EGFP gene, and the target peptide complex inserted CD9 encoding gene, wherein the target peptide is selected from but not limited to angiopeptin-2, ApoB, ApoE, VCAM-1 internalization sequence and striated muscle target peptide. The said vector is introduced into exosome-producing cells such as HEK293T cells to obtain exosomes with target peptide labeled in the membrane protein (FIG. 1). FIGS. 2 and 5 shows the expression of the target peptide in exosome membrane protein.

EXAMPLE

Hereinafter, the present invention will be described in detail with reference to the following examples. However, the following examples are illustrative of the present invention, and the content of the present invention is not limited thereto.

Example 1. Preparation of Exosomes Labeled with Angiopeptin-2 Peptide Complex in Exosomal Membrane Protein Angiopeptin-2 is a protein targeting the blood-brain barrier. An exosome labeled with the Angiopeptin-2 peptide in the exosome membrane protein was prepared by the following method.

First, a multicloning site of pSF-CMV-CMV-Sbfl vector (#OG411, Oxford Genetics, UK), Ndel, was digested with Ndel restriction enzyme to linearize the DNA. Thereafter, the CIBN gene (SEQ ID NO: 1), the EGFP gene (SEQ ID NO: 2), a gene fragment of CD9 encoding 1-170 amino acids from the N-terminal, a gene fragment of CD9 encoding 171-228 amino acids from the N-terminal, and a gene fragment encoding the angiopeptin-2 peptide complex (SEQ ID NO: 4) was prepared by PCR. Next, the Ndel portion of the pSF-CMV-CMV-Sbfl vector was sequentially connected by Gibson assembly so that the two ends of the three fragments were overlapped with each other by 20 to 24 bp in order to obtain vector having a sequence of CIBN-EGFP-CD9 (1-170)-angiopeptin-2 peptide complex-CD9(171-228). The angiopeptin-2 peptide complex is consisting with three repeated angiopeptin-2 amino acid sequences (SEQ ID NO: 5), and a linker described by the amino acid sequence of GGGGS (SEQ ID NO: 6) is located between angiopeptin-2 amino acid sequences, and a linker described in the amino acid sequence of PPVAT (SEQ ID NO: 7) is inserted at both ends of the angiopeptin-2 sequences.

The vector encoding CIBN-EGFP-CD9 (1-170)-angiopeptin 2 complex-CD9 (171-228) was introduced into HEK293T cells as exosome-producing cells. 24 hours incubation was followed by 48 hours incubation in the media without fetal bovine serum. The culture was centrifuged at 1,000 rpm for 3 minutes and was filtered using a polyethersulfone membrane having a pore size of 0.2 μm. The filtrate was first concentrated through tangential flow filtration at 4° C. The concentrate was then purified using size exclusion chromatography with a sepharose bead at 4° C. 300 to 500 ml of a phosphate buffered saline was added to dilute the solution, followed by secondary concentration through tangential flow filtration at 4° C. to obtained exosomes labeled with angiopeptin-2 peptide in the exosomal membrane.

Example 2. Preparation of Exosomes Labeled with ApoB Peptide Complex in Exosomal Membrane The ApoB is a protein targeting the blood-brain barrier, and the exosome labeled with the ApoB peptide complex in the exosomal membrane was prepared by the following method.

The same steps described in Example 1 were carried out, except only the ApoB peptide complex (SEQ ID NO: 8) was inserted to obtain the exosome labeled with the ApoB peptide complex in the exosomal membrane. The ApoB peptide complex is consisting with three repeated ApoB amino acid sequences (SEQ ID NO: 9), and the linker described by the amino acid sequence of GGGGS (SEQ ID NO: 6) is located between ApoB amino acid sequences, and the linker described in the amino acid sequence of PPVAT (SEQ ID NO: 7) is inserted at both ends of the ApoB sequences.

Example 3. Preparation of Exosomes Labeled with ApoE Peptide Complex in Exosomal Membrane The ApoE is a protein targeting the blood-brain barrier, and the exosome labeled with the ApoE peptide complex in exosomal membrane was prepared by the following method.

The same steps described in Example 1 were carried out, except only the ApoE peptide complex (SEQ ID NO: 10) was inserted to obtain the exosome labeled with the ApoE peptide complex in the exosomal membrane. The ApoE peptide complex is consisting with three repeated ApoE amino acid sequences (SEQ ID NO: 11), and the linker described by the amino acid sequence of GGGGS (SEQ ID NO: 6) is located between ApoE amino acid sequences, and the linker described in the amino acid sequence of PPVAT (SEQ ID NO: 7) is inserted at both ends of the ApoE sequences.

Example 4. Production of Exosomes Labeled with VCAM-1 Internalization Sequence Peptide Complex in Exosomal Membrane The VCAM-1 (vascular cell adhesion molecule-1) is a protein targeting the vascular inflammation site, and the exosome labeled with VCAM-1 internalization sequence peptide complex in the exosomal membrane was prepared by the following method.

The same steps described in Example 1 were carried out, except only the VCAM-1 internalization sequence peptide complex (SEQ ID NO: 12) was inserted to obtain the exosome labeled with the VCAM-1 internalization sequence peptide complex in the exosomal membrane. The VCAM-1 internalization sequence peptide complex is consisting with three repeated VCAM-1 internalization amino acid sequences (SEQ ID NO: 13), and the linker described by the amino acid sequence of GGGGS (SEQ ID NO: 6) is located between VCAM-1 internalization sequences, and the linker described in the amino acid sequence of PPVAT (SEQ ID NO: 7) is inserted at both ends of the VCAM-1 internalization sequences.

Example 5. Preparation of Exosomes Labeled with Striated Muscle Target Peptide Complex in Exosomal Membrane The striated muscle target peptide is a protein targeting striated muscle, and the exosome labeled with the straited muscle target peptide in the exosomal membrane was prepared by the following method.

The same steps described in Example 1 were carried out, except only the striated muscle target peptide complex (SEQ ID NOs: 14-16) was inserted to obtain the exosome labeled with the striated muscle target peptide complex in the exosomal membrane. Striated muscle target peptide complexes are consisting with three repeated amino acid sequence, ASSLNIA (SEQ ID NO: 17), TARGEHKEEELI (SEQ ID NO: 18) or SKTFNTHPQSTP (SEQ ID NO: 19), the linker described by the amino acid sequence of GGGGS (SEQ ID NO: 6) is located between sequences, and the linker described in the amino acid sequence of PPVAT (SEQ ID NO: 7) is inserted at both ends of the sequences.

Example 6. Expression of Angiopopein-2 Peptide Complex

The exosome of Example 1 was transfected to HEK293T cells. The expression of the angioprotein-2 peptide complex in the exosomal membrane was confirmed through a fluorescence microscope after 24 hours. FIG. 2 shows the expression of the angioprotein-2 peptide complex in the exosomal membrane.

Example 7. Expression of ApoB Peptide Complex

Figure 3:
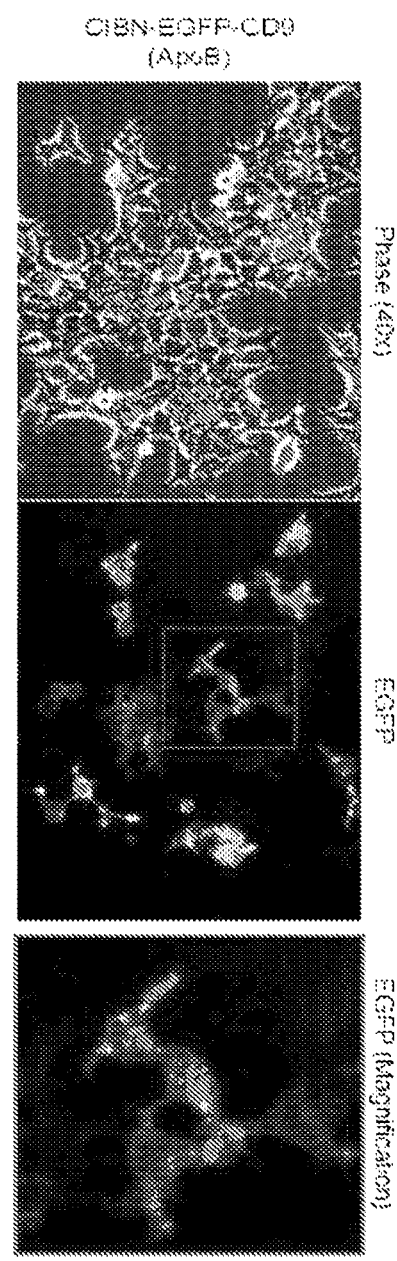
FIG. 3 is an image showing the expression of an ApoB peptide complex in HEK293T cells treated with the exosome comprising the ApoB peptide complex.

The exosome of Example 2 was transfected to HEK293T cells. The expression of the ApoB peptide complex in the exosomal membrane was confirmed through the fluorescence microscope after 24 hours. FIG. 3 shows the expression of the ApoB peptide complex in the exosomal membrane.

Example 8. Expression of ApoE Peptide Complex

Figure 4:
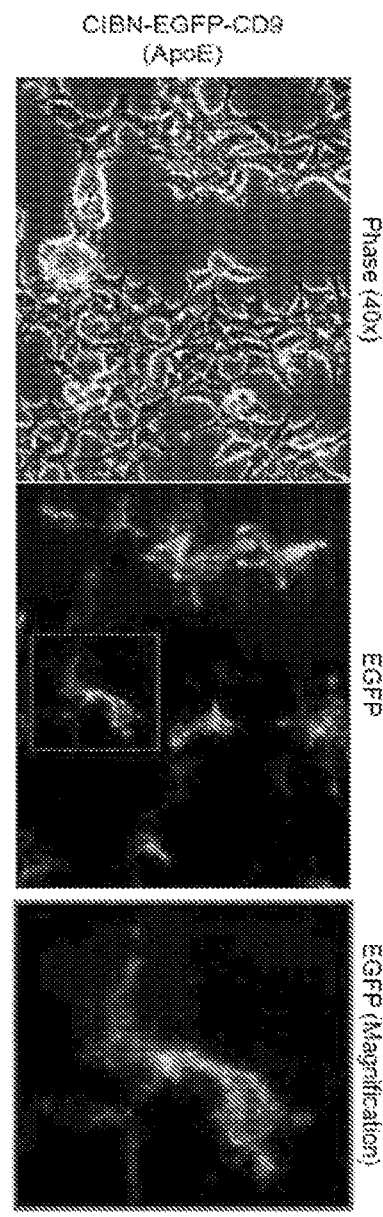
FIG. 4 is an image showing the expression of an ApoE peptide complex in HEK293T cells treated with the exosome comprising the ApoE peptide complex.

The exosome of Example 3 was transfected to HEK293T cells. The expression of the ApoE peptide complex in the exosomal membrane was confirmed through the fluorescence microscope after 24 hours. FIG. 4 shows the expression of the ApoE peptide complex in the exosomal membrane.

Example 9. Expression of VCAM-1 Internalization Sequence Peptide Complex

The exosome of Example 4 was transfected to HEK293T cells. The expression of the VCAM-1 internalization sequence peptide complex in the exosomal membrane was confirmed through the fluorescence microscope after 24 hours. FIG. 5 shows the expression of the VCAM-1 internalization sequence peptide complex in the exosomal membrane.

Example 10. Expression of Striated Muscle Target Peptide Complex

The exosome of Example 5 was transfected to HEK293T cells. The expression of the striated muscle target peptide complex in the exosomal membrane was confirmed through the fluorescence microscope after 24 hours. The expression of the striated muscle target peptide complex in the exosomal membrane was confirmed.

Example 11. Target-Specific Delivery of Exosomes Labeled with Angiopeptin-2 Peptide Complex on Exosomal Membrane The vector encoding CIBN-EGFP-CD9(1-170)-angiopeptin 2 peptide complex-CD9(171-228) was obtained with the same steps described in Example 1, except that an additional Cre recombinase-CRY2 gene was further inserted under an LED emitting light of 460 nm at an intensity of 100 μW. The vector was introduced to HEK293T as the exosome production cell. 24 hours incubation was followed by 48 hours incubation in the media without fetal bovine serum under the LED light. The culture medium was separated by tangential flow filtration and size exclusion chromatography to obtain exosomes labeled with the angiopeptin-2 peptide complex in the exosomal membrane. An exosome in which angiopeptin-2 peptide complex was not labeled on the exosomal membrane was used as a control group. The resulting exosome at a concentration of 1×10$^9$ particles/50 μl was injected intravenously or intraperitoneally into the blood vessels of C57BL/6 loxP-eNphr3.0-loxP-eYFP TG mice (The Jackson Laboratory, Bar Harbor, Maine, USA) and organs were excised and histo-pathologically examined 48 or 72 hours after the injection. The distribution of eYFP in mice was analyzed to determine the function and distribution of the exosome labeled with the specific target peptide in vivo.

As a result, the exosome labeled with the angiopeptin-2 peptide was specifically transferred to the blood brain barrier.

Example 12. Target-Specific Delivery Effect of Exosome Labeled with ApoB Peptide Complex in Exosomal Membrane The vector encoding CIBN-EGFP-CD9(1-170)-ApoB peptide complex-CD9(171-228) was obtained the same steps described in Example 2, except that the additional Cre recombinase-CRY2 gene was further inserted under the LED emitting light of 460 nm at the intensity of 100 μW. Same steps described in Example 11 were carried out to determine the function and the distribution of the exosome labeled with the specific target peptide in vivo.

As a result, the exosome labeled with the ApoB peptide complex was specifically transferred to the blood brain barrier.

Example 13. Target-Specific Delivery Effect of Exosome Labeled with ApoE Peptide Complex in Exosomal Membrane The vector encoding CIBN-EGFP-CD9(1-170)-ApoE peptide complex-CD9(171-228) was obtained the same steps described in Example 3, except that the additional Cre recombinase-CRY2 gene was further inserted under the LED emitting light of 460 nm at the intensity of 100 μW. Same steps described in Example 11 were carried out to determine the function and the distribution of the exosome labeled with the specific target peptide in vivo.

As a result, the exosome labeled with the ApoE peptide complex was specifically transferred to the blood brain barrier.

Example 14. Target-Specific Delivery Effect of Exosome Labeled with VCAM-1 Internalization Sequence Peptide Complex in Exosomal Membrane The vector encoding CIBN-EGFP-CD9(1-170)-VCAM-1 internalization sequence peptide complex-CD9(171-228) was obtained the same steps described in Example 4, except that the additional Cre recombinase-CRY2 gene was further inserted under the LED emitting light of 460 nm at the intensity of 100 μW. Same steps described in Example 11 were carried out to determine the function and the distribution of the exosome labeled with the specific target peptide in vivo.

As a result, it was confirmed that the exosome labeled with the VCAM-1 internalization sequence peptide complex in the membrane protein was specifically transferred to the site of vascular inflammation.

Example 15. Target-Specific Delivery Effect of Exosome Labeled with Striated Muscle Target Peptide Complex in Exosomal Membrane The vector encoding CIBN-EGFP-CD9(1-170)-striated muscle target peptide complex-CD9(171-228) was obtained the same steps described in Example 5, except that the additional Cre recombinase-CRY2 gene was further inserted under the LED emitting light of 460 nm at the intensity of 100 μW. Same steps described in Example 11 were carried out to determine the function and the distribution of the exosome labeled with the specific target peptide in vivo.

As a result, it was confirmed that exosome labeled with the striated muscle target peptide complex in the membrane protein was specifically transferred to the striated muscle.

```
                        SEQUENCE LISTING

Sequence total quantity: 84
SEQ ID NO: 1            moltype = AA  length = 317
FEATURE                 Location/Qualifiers
source                  1..317
                        mol_type = protein
                        organism = Homo sapiens
SEQUENCE: 1
MFQAAERPQE WAMEGPRDGL KKERLLDDRH DSGLDSMKDE EYEQMVKELQ EIRLEPQEVP  60
RGSEPWKQQL TEDGDSFLHL AIIHEEKALT MEVIRQVKGD LAFLNFQNNL QQTPLHLAVI 120
TNQPEIAEAL LGAGCDPELR DFRGNTPLHL ACEQGCLASV GVLTQSCTTP HLHSILKATN 180
YNGHTCLHLA SIHGYLGIVE LLVSLGADVN AQEPCNGRTA LHLAVDLQNP DLVSLLLKCG 240
ADVNRVTYQG YSPYQLTWGR PSTRIQQQLG QLTLENLQML PESEDEESYD TESEFTEFTE 300
DELPYDDCVF GGQRLTL                                               317

SEQ ID NO: 2            moltype = AA  length = 356
FEATURE                 Location/Qualifiers
source                  1..356
                        mol_type = protein
                        organism = Homo sapiens
SEQUENCE: 2
MAGVACLGKA ADADEWCDSG LGSLGPDAAA PGGPGLGAEL GPGLSWAPLV FGYVTEDGDT  60
```

```
ALHLAVIHQH EPFLDFLLGF SAGTEYMDLQ NDLGQTALHL AAILGETSTV EKLYAAGAGL   120
CVAERRGHTA LHLACRVGAH ACARALLQPR PRRPREAPDT YLAQGPDRTP DTNHTPVALY   180
PDSDLEKEEE ESEEDWKLQL EAENYEGHTP LHVAVIHKDV EMVRLLRDAG ADLDKPEPTC   240
GRSPLHLAVE AQAADVLELL LRAGANPAAR MYGGRTPLGS AMLRPNPILA RLLRAHGAPE   300
PEGEDEKSGP CSSSSDSDSG DEGDEYDDIV VHSSRSQTRL PPTPASKPLP DDPRPV       356

SEQ ID NO: 3              moltype = AA   length = 500
FEATURE                   Location/Qualifiers
source                    1..500
                          mol_type = protein
                          organism = Homo sapiens
SEQUENCE: 3
MNQRRSESRP GNHRLQAYAE PGKGDSGGAG PLSGSARRGR GGGGAIRVRR PCWSGGAGRG    60
GGPAWAVRLP TVTAGWTWPA LRTLSSLRAG PSEPHSPGRR PPRAGRPLCQ ADPQPGKAAR   120
RSLEPDPAQT GPRPARAAGM SEARKGPDEA EESQYDSGIE SLRSLRSLPE STSAPASGPS   180
DGSPQPCTHP PGPVKEPQEK EDADGERADS TYGSSSLTYT LSLLGGPEAE DPAPRLPLPH   240
VGALSPQQLE ALTYISEDGD TLVHLAVIHE APAVLLCCLA LLPQEVLDIQ NNLYQTALHL   300
AVHLDQPGAV RALVLKGASR ALQDRHGDTA LHVACQRGTL ACARCLLEGR PEPGRGTSHS   360
LDLQLQNWQG LACLHIATLQ KNQPLMELLL RNGADIDVQE GTSGKTALHL AVETQERGLV   420
QFLLQAGAQV DARMLNGCTP LHLAAGRGLM GISSTLCKAG ADSLLRNVED ETPQDLTEES   480
LVLLPFDDLK ISGKLLLCTD                                               500

SEQ ID NO: 4              moltype = AA   length = 454
FEATURE                   Location/Qualifiers
source                    1..454
                          mol_type = protein
                          organism = Homo sapiens
SEQUENCE: 4
MPRCPAGAMD EGPVDLRTRP KAAGLPGAAL PLRKRPLRAP SPEPAAPRGA AGLVVPLDPL    60
RGGCDLPAVP GPPHGLARPE ALYYPGALLP LYPTRAMGSP FPLVNLPTPL YPMMCPMEHP   120
LSADIAMATR ADEDGDTPLH IAVVQGNLPA VHRLVNLFQQ GGRELDIYNN LRQTPLHLAV   180
ITTLPSVVRL LVTAGASPMA LDRHGQTAAH LACEHRSPTC LRALLDSAAP GTLDLEARNY   240
DGLTALHVAV NTECQETVQL LLERGADIDA VDIKSGRSPL IHAVENNSLS MVQLLLQHGA   300
NVNAQMYSGS SALHSASGRG LLPLVRTLVR SGADSSLKNC HNDTPLMVAR SRRVIDILRG   360
KATRPASTSQ PDPSPDRSAN TSPESSSRLS SNGLLSASPS SSPSQSPPRD PPGFPMAPPN   420
FFLPSPSPPA FLPFAGVLRG PGRPVPPSPA PGGS                               454

SEQ ID NO: 5              moltype = AA   length = 317
FEATURE                   Location/Qualifiers
source                    1..317
                          mol_type = protein
                          organism = Homo sapiens
SEQUENCE: 5
MFQAAERPQE WAMEGPRDGL KKERLLDDRH DAGLDAMKDE EYEQMVKELQ EIRLEPQEVP    60
RGSEPWKQQL TEDGDSFLHL AIIHEEKALT MEVIRQVKGD LAFLNFQNNL QQTPLHLAVI   120
TNQPEIAEAL LGAGCDPELR DFRGNTPLHL ACEQGCLASV GVLTQSCTTP HLHSILKATN   180
YNGHTCLHLA SIHGYLGIVE LLVSLGADVN AQEPCNGRTA LHLAVDLQNP DLVSLLLKCG   240
ADVNRVTYQG YSPYQLTWGR PSTRIQQQLG QLTLENLQML PESEDEESYD TESEFTEFTE   300
DELPYDDCVF GGQRLTL                                                  317

SEQ ID NO: 6              moltype = AA   length = 192
FEATURE                   Location/Qualifiers
source                    1..192
                          mol_type = protein
                          organism = Homo sapiens
SEQUENCE: 6
MDGSGEQPRG GGPTSSEQIM KTGALLLQGF IQDRAGRMGG EAPELALDPV PQDASTKKLS    60
ECLKRIGDEL DSNMELQRMI AAVDTDSPRE VFFRVAADMF SDGNFNWGRV VALFYFASKL   120
VLKALCTKVP ELIRTIMGWT LDFLRERLLG WIQDQGGWDG LLSYFGTPTW QTVTIFVAGV   180
LTASLTIWKK MG                                                       192

SEQ ID NO: 7              moltype = AA   length = 199
FEATURE                   Location/Qualifiers
source                    1..199
                          mol_type = protein
                          organism = Homo sapiens
SEQUENCE: 7
MSSGNAKIGH PAPNFKATAV MPDGQFKDIS LSDYKGKYVV FFFYPLDFTF VCPTEIIAFS    60
DRAEEFKKLN CQVIGASVDS HFCHLAWVNT PKKQGGLGPM NIPLVSDPKR TIAQDYGVLK   120
ADEGISFRGL FIIDDKGILR QITVNDLPVG RSVDETLRLV QAFQFTDKHG EVCPAGWKPG   180
SDTIKPDVQK SKEYFSKQK                                                199

SEQ ID NO: 8              moltype = AA   length = 198
FEATURE                   Location/Qualifiers
source                    1..198
                          mol_type = protein
                          organism = Homo sapiens
SEQUENCE: 8
MASGNARIGK PAPDFKATAV VDGAFKEVKL SDYKGKYVVL FFYPLDFTFV CPTEIIAFSN    60
```

-continued

```
RAEDFRKLGC EVLGVSVDSQ FTHLAWINTP RKEGGLGPLN IPLLADVTRR LSEDYGVLKT  120
DEGIAYRGLF IIDGKGVLRQ ITVNDLPVGR SVDEALRLVQ AFQYTDEHGE VCPAGWKPGS  180
DTIKPNVDDS KEYFSKHN                                                198

SEQ ID NO: 9           moltype = AA  length = 343
FEATURE                Location/Qualifiers
source                 1..343
                       mol_type = protein
                       organism = Bacteriophage P1
SEQUENCE: 9
MSNLLTVHQN LPALPVDATS DEVRKNLMDM FRDRQAFSEH TWKMLLSVCR SWAAWCKLNN  60
RKWFPAEPED VRDYLLYLQA RGLAVKTIQQ HLGQLNMLHR RSGLPRPSDS NAVSLVMRRI  120
RKENVDAGER AKQALAFERT DFDQVRSLME NSDRCQDIRN LAFLGIAYNT LLRIAEIARI  180
RVKDISRTDG GRMLIHIGRT KTLVSTAGVE KALSLGVTKL VERWISVSGV ADDPNNYLFC  240
RVRKNGVAAP SATSQLSTRA LEGIFEATHR LIYGAKDDSG QRYLAWSGHS ARVGAARDMA  300
RAGVSIPEIM QAGGWTNVNI VMNYIRNLDS ETGAMVRLLE DGD                    343

SEQ ID NO: 10          moltype = AA  length = 469
FEATURE                Location/Qualifiers
source                 1..469
                       mol_type = protein
                       organism = Streptococcus pyogenes
SEQUENCE: 10
MHSFPPLLLL LFWGVVSHSF PATLETQEQD VDLVQKYLEK YYNLKNDGRQ VEKRRNSGPV  60
VEKLKQMQEF FGLKVTGKPD AETLKVMKQP RCGVPDVAQF VLTEGNPRWE QTHLTYRIEN  120
YTPDLPRADV DHAIEKAFQL WSNVTPLTFT KVSEGQADIM ISFVRGDHRD NSPFDGPGGN  180
LAHAFQPGPG IGGDAHFDED ERWTNNFREY NLHRVAAHEL GHSLGLSHST DIGALMYPSY  240
TFSGDVQLAQ DDIDGIQAIY GRSQNPVQPI GPQTPKACDS KLTFDAITTI RGEVMFFKDR  300
FYMRTNPFYP EVELNFISVF WPQLPNGLEA AYEFADRDEV RFFKGNKYWA VQGQNVLHGY  360
PKDIYSSFGF PRTVKHIDAA LSEENTGKTY FFVANKYWRY DEYKRSMDPG YPKMIAHDFP  420
GIGHKVDAVF MKDGFFYFFH GTRQYKFDPK TKRILTLQKA NSWFNCRKN              469

SEQ ID NO: 11          moltype = AA  length = 1300
FEATURE                Location/Qualifiers
source                 1..1300
                       mol_type = protein
                       organism = Francisella tularensis
SEQUENCE: 11
MSIYQEFVNK YSLSKTLRFE LIPQGKTLEN IKARGLILDD EKRAKDYKKA KQIIDKYHQF  60
FIEEILSSVC ISEDLLQNYS DVYFKLKKSD DDNLQKDFKS AKDTIKKQIS EYIKDSEKFK  120
NLFNQNLIDA KKGQESDLIL WLKQSKDNGI ELFKANSDIT DIDEALEIIK SFKGWTTYFK  180
GFHENRKNVY SSNDIPTSII YRIVDDNLPK FLENKAKYES LKDKAPEAIN YEQIKKDLAE  240
ELTFDIDYKT SEVNQRVFSL DEVFEIANFN NYLNQSGITK FNTIIGGKFV NGENTKRKGI  300
NEYINLYSQQ INDKTLKKYK MSVLFKQILS DTESKSFVID KLEDDSDVVT TMQSFYEQIA  360
AFKTVEEKSI KETLSLLFDD LKAQKLDLSK IYFKNDKSLT DLSQQVFDDY SVIGTAVLEY  420
ITQQIAPKNL DNPSKKEQEL IAKKTEKAKY LSLETIKLAL EEFNKHRDID KQCRFEEILA  480
NFAAIPMIFD EIAQNKDNLA QISIKYQNQG KKDLLQASAE DDVKAIKDLL DQTNNLLHKL  540
KIFHISQSED KANILDKDEH FYLVFEECYF ELANIVPLYN KIRNYITQKP YSDEKFKLNF  600
ENSTLANGWD KNKEPDNTAI LFIKDDKYYL GVMNKKNNKI FDDKAIKENK GEGYKKIVYK  660
LLPGANKMLP KVFFSAKSIK FYNPSEDILR IRNHSTHTKN GSPQKGYEKF EFNIEDCRKF  720
IDFYKQSISK HPEWKDFGFR FSDTQRYNSI DEFYREVENQ GYKLTFENIS ESYIDSVVNQ  780
GKLYLFQIYN KDFSAYSKGR PNLHTLYWKA LFDERNLQDV VYKLNGEAEL FYRKQSIPKK  840
ITHPAKEAIA NKNKDNPKKE SVFEYDLIKD KRFTEDKFFF HCPITINFKS SGANKFNDEI  900
NLLLKEKAND VHILSIDRGE RHLAYYTLVD GKGNIIKQDT FNIIGNDRMK TNYHDKLAAI  960
EKDRDSARKD WKKINNIKEM KEGYLSQVVH EIAKLVIEYN AIVVFEDLNF GFKRGRFKVE  1020
KQVYQKLEKM LIEKLNYLVF KDNEFDKTGG VLRAYQLTAP FETFKKMGKQ TGIIYYVPAG  1080
FTSKICPVTG FVNQLYPKYE SVSKSQEFFS KFDKICYNLD KGYFEFSFDY KNFGDKAAKG  1140
KWTIASFGSR LINFRNSDKN HNWDTREVYP TKELEKLLKD YSIEYGHGEC IKAAICGESD  1200
KKFFAKLTSV LNTILQMRNS KTGTELDYLI SPVADVNGNF FDSRQAPKNM PQDADANGAY  1260
HIGLKGLMLL GRIKNNQEGK KLNLVIKNEE YFEFVQNRNN                        1300

SEQ ID NO: 12          moltype = AA  length = 536
FEATURE                Location/Qualifiers
source                 1..536
                       mol_type = protein
                       organism = Homo sapiens
SEQUENCE: 12
MEFSSPSREE CPKPLSRVSI MAGSLTGLLL LQAVSWASGA RPCIPKSFGY SSVVCVCNAT  60
YCDSFDPPTF PALGTFSRYE STRSGRRMEL SMGPIQANHT GTGLLLTLQP EQKFQKVKGF  120
GGAMTDAAAL NILALSPPAQ NLLLKSYFSE EGIGYNIIRV PMASCDFSIR TYTYADTPDD  180
FQLHNFSLPE EDTKLKIPLI HRALQLAQRP VSLLASPWTS PTWLKTNGAV NGKGSLKGQP  240
GDIYHQTWAR YFVKFLDAYA EHKLQFWAVT AENEPSAGLL SGYPFQCLGF TPEHQRDFIA  300
RDLGPTLANS THHNVRLLML DDQRLLLPHW AKVVLTDPEA AKYVHGIAVH WYLDFLAPAK  360
ATLGETHRLF PNTMLFASEA CVGSKFWEQS VRLGSWDRGM QYSHSIITNL LYHVVGWTDW  420
NLALNPEGGP NWVRNFVDSP IIVDITKDTF YKQPMFYHLG HFSKFIPEGS QRVGLVASQK  480
NDLDAVALMH PDGSAVVVVL NRSSKDVPLT IKDPAVGFLE TISPGYSIHT YLWRRQ      536

SEQ ID NO: 13          moltype = AA  length = 469
FEATURE                Location/Qualifiers
```

```
source                  1..469
                        mol_type = protein
                        organism = Homo sapiens
SEQUENCE: 13
MHSFPPLLLL LFWGVVSHSF PATLETQEQD VDLVQKYLEK YYNLKNDGRQ VEKRRNSGPV    60
VEKLKQMQEF FGLKVTGKPD AETLKVMKQP RCGVPDVAQF VLTEGNPRWE QTHLTYRIEN   120
YTPDLPRADV DHAIEKAFQL WSNVTPLTFT KVSEGQADIM ISFVRGDHRD NSPFDGPGGN   180
LAHAFQPGPG IGGDAHFDED ERWTNNFREY NLHRVAAHEL GHSLGLSHST DIGALMYPSY   240
TFSGDVQLAQ DDIDGIQAIY GRSQNPVQPI GPQTPKACDS KLTFDAITTI RGEVMFFKDR   300
FYMRTNPFYP EVELNFISVF WPQLPNGLEA AYEFADRDEV RFFKGNKYWA VQGQNVLHGY   360
PKDIYSSFGF PRTVKHIDAA LSEENTGKTY FFVANKYWRY DEYKRSMDPG YPKMIAHDFP   420
GIGHKVDAVF MKDGFFYFFH GTRQYKFDPK TKRILTLQKA NSWFNCRKN              469

SEQ ID NO: 14           moltype = AA    length = 207
FEATURE                 Location/Qualifiers
source                  1..207
                        mol_type = protein
                        organism = Homo sapiens
SEQUENCE: 14
MAPFEPLASG ILLLLWLIAP SRACTCVPPH PQTAFCNSDL VIRAKFVGTP EVNQTTLYQR    60
YEIKMTKMYK GFQALGDAAD IRFVYTPAME SVCGYFHRSH NRSEEFLIAG KLQDGLLHIT   120
TCSFVAPWNS LSLAQRRGFT KTYTVGCEEC TVFPCLSIPC KLQSGTHCLW TDQLLQGSEK   180
GFQSRHLACL PREPGLCTWQ SLRSQIA                                      207

SEQ ID NO: 15           moltype = AA    length = 220
FEATURE                 Location/Qualifiers
source                  1..220
                        mol_type = protein
                        organism = Homo sapiens
SEQUENCE: 15
MGAAARTLRL ALGLLLLATL LRPADACSCS PVHPQQAFCN ADVVIRAKAV SEKEVDSGND    60
IYGNPIKRIQ YEIKQIKMFK GPEKDIEFIY TAPSSAVCGV SLDVGGKKEY LIAGKAEGDG   120
KMHITLCDFI VPWDTLSTTQ KKSLNHRYQM GCECKITRCP MIPCYISSPD ECLWMDWVTE   180
KNINGHQAKF FACIKRSDGS CAWYRGAAPP KQEFLDIEDP                        220

SEQ ID NO: 16           moltype = AA    length = 211
FEATURE                 Location/Qualifiers
source                  1..211
                        mol_type = protein
                        organism = Homo sapiens
SEQUENCE: 16
MTPWLGLIVL LGSWSLGDWG AEACTCSPSH PQDAFCNSDI VIRAKVVGKK LVKEGPFGTL    60
VYTIKQMKMY RGFTKMPHVQ YIHTEASESL CGLKLEVNKY QYLLTGRVYD GKMYTGLCNF   120
VERWDQLTLS QRKGLNYRYH LGCNCKIKSC YYLPCFVTSK NECLWTDMLS NFGYPGYQSK   180
HYACIRQKGG YCSWYRGWAP PDKSIINATD P                                 211

SEQ ID NO: 17           moltype = AA    length = 224
FEATURE                 Location/Qualifiers
source                  1..224
                        mol_type = protein
                        organism = Homo sapiens
SEQUENCE: 17
MPGSPRPAPS WVLLLRLLAL LRPPGLGEAC SCAPAHPQQH ICHSALVIRA KISSEKVVPA    60
SADPADTEKM LRYEIKQIKM FKGFEKVKDV QYIYTPFDSS LCGVKLEANS QKQYLLTGQV   120
LSDGKVFIHL CNYIEPWEDL SLVQRESLNH HYHLNCGCQI TTCYTVPCTI SAPNECLWTD   180
WLLERKLYGY QAQHYVCMKH VDGTCSWYRG HLPLRKEFVD IVQP                   224

SEQ ID NO: 18           moltype = AA    length = 404
FEATURE                 Location/Qualifiers
source                  1..404
                        mol_type = protein
                        organism = Homo sapiens
SEQUENCE: 18
MADKVLKEKR KLFIRSMGEG TINGLLDELL QTRVLNKEEM EKVKRENATV MDKTRALIDS    60
VIPKGAQACQ ICITYICEED SYLAGTLGLS ADQTSGNYLN MQDSQGVLSS FPAPQAVQDN   120
PAMPTSSGSE GNVKLCSLEE AQRIWKQKSA EIYPIMDKSS RTRLALIICN EEFDSIPRRT   180
GAEVDITGMT MLLQNLGYSV DVKKNLTASD MTTELEAFAH RPEHKTSDST FLVFMSHGIR   240
EGICGKKHSE QVPDILQLNA IFNMLNTKNC PSLKDKPKVI IIQACRGDSP GVVWFKDSVG   300
VSGNLSLPTT EEFEDDAIKK AHIEKDFIAF CSSTPDNVSW RHPTMGSVFI GRLIEHMQEY   360
ACSCDVEEIF RKVRFSFEQP DGRAQMPTTE RVTLTRCFYL FPGH                   404

SEQ ID NO: 19           moltype = AA    length = 452
FEATURE                 Location/Qualifiers
source                  1..452
                        mol_type = protein
                        organism = Homo sapiens
SEQUENCE: 19
MAAPSAGSWS TFQHKELMAA DRGRRILGVC GMHPHHQETL KKNRVVLAKQ LLLSELLEHL    60
LEKDIITLEM RELIQAKVGS FSQNVELLNL LPKRGPQAFD AFCEALRETK QGHLEDMLLT   120
```

```
TLSGLQHVLP PLSCDYDLSL PFPVCESCPL YKKLRLSTDT VEHSLDNKDG PVCLQVKPCT    180
PEFYQTHFQL AYRLQSRPRG LALVLSNVHF TGEKELEFRS GGDVDHSTLV TLFKLLGYDV    240
HVLCDQTAQE MQEKLQNFAQ LPAHRVTDSC IVALLSHGVE GAIYGVDGKL LQLQEVFQLF    300
DNANCPSLQN KPKMFFIQAC RGDETDRGVD QQDGKNHAGS PGCEESDAGK EKLPKMRLPT    360
RSDMICGYAC LKGTAAMRNT KRGSWYIEAL AQVFSERACD MHVADMLVKV NALIKDREGY    420
APGTEFHRCK EMSEYCSTLC RHLYLFPGHP PT                                 452

SEQ ID NO: 20           moltype = AA  length = 277
FEATURE                 Location/Qualifiers
source                  1..277
                        mol_type = protein
                        organism = Homo sapiens
SEQUENCE: 20
MENTENSVDS KSIKNLEPKI IHGSESMDSG ISLDNSYKMD YPEMGLCIII NNKNFHKSTG     60
MTSRSGTDVD AANLRETFRN LKYEVRNKND LTREEIVELM RDVSKEDHSK RSSFVCVLLS    120
HGEEGIIFGT NGPVDLKKIT NFFRGDRCRS LTGKPKLFII QACRGTELDC GIETDSGVDD    180
DMACHKIPVE ADFLYAYSTA PGYYSWRNSK DGSWFIQSLC AMLKQYADKL EFMHILTRVN    240
RKVATEFESF SFDATFHAKK QIPCIVSMLT KELYFYH                            277

SEQ ID NO: 21           moltype = AA  length = 377
FEATURE                 Location/Qualifiers
source                  1..377
                        mol_type = protein
                        organism = Homo sapiens
SEQUENCE: 21
MAEGNHRKKP LKVLESLGKD FLTGVLDNLV EQNVLNWKEE EKKKYYDAKT EDKVRVMADS     60
MQEKQRMAGQ MLLQTFFNID QISPNKKAHP NMEAGPPESG ESTDALKLCP HEEFLRLCKE    120
RAEEIYPIKE RNNNTRLALI ICNTEFDHLP PRNGADFDIT GMKELLEGLD YSVDVEENLT    180
ARDMESALRA FATRPEHKSS DSTFLVLMSH GILEGICGTV HDEKKPDVLL YDTIFQIFNN    240
RNCLSLKDKP KVIIVQACRG ANRGELWVRD SPASLEVASS QSSENLEEDA VYKTHVEKDF    300
IAFCSSTPHN VSWRDMGS IFITQLITCF QKYSWCCHLE EVFRKVQQSF ETPRAKAQMP    360
TIERLSMTRY FYLFPGN                                                 377

SEQ ID NO: 22           moltype = AA  length = 434
FEATURE                 Location/Qualifiers
source                  1..434
                        mol_type = protein
                        organism = Homo sapiens
SEQUENCE: 22
MAEDSGKKKR RKNFEAMFKG ILQSGLDNFV INHMLKNNVA GQTSIQTLVP NTDQKSTSVK     60
KDNHKKKTVK MLEYLGKDVL HGVFNYLAKH DVLTLKEEEK KKYYDTKIED KALILVDSLR    120
KNRVAHQMFT QTLLNMDQKI TSVKPLLQIE AGPPESAEST NILKLCPREE FLRLCKKNHD    180
EIYPIKKRED RRRLALIICN TKFDHLPARN GAHYDIVGMK RLLQGLGYTV VDEKNLTARD    240
MESVLRAFAA RPEHKSSDST FLVLMSHGIL EGICGTAHKK KKPDVLLYDT IFQIFNNRNC    300
LSLKDKPKVI IVQACRGEKH GELWVRDSPA SLALISSQSS ENLEADSVCK IHEEKDFIAF    360
CSSTPHNVSW RDRTRGSIFI TELITCFQKY SCCCHLMEIF RKVQKSFEVP QAKAQMPTIE    420
RATLTRDFYL FPGN                                                    434

SEQ ID NO: 23           moltype = AA  length = 293
FEATURE                 Location/Qualifiers
source                  1..293
                        mol_type = protein
                        organism = Homo sapiens
SEQUENCE: 23
MSSASGLRRG HPAGGEENMT ETDAFYKREM FDPAEKYKMD HRRRGIALIF NHERFFWHLT     60
LPERRGTCAD RDNLTRRFSD LGFEVKCFND LKAEELLLKI HEVSTVSHAD ADCFVCVFLS    120
HGEGNHIYAY DAKIEIQTLT GLFKGDKCHS LVGKPKIFII QACRGNQHDV PVIPLDVVDN    180
QTEKLDTNIT EVDAASVYTL PAGADFLMCY SVAEGYYSHR ETVNGSWYIQ DLCEMLGKYG    240
SSLEFTELLT LVNRKVSQRR VDFCKDPSAI GKKQVPCFAS MLTKKLHFFP KSN           293

SEQ ID NO: 24           moltype = AA  length = 303
FEATURE                 Location/Qualifiers
source                  1..303
                        mol_type = protein
                        organism = Homo sapiens
SEQUENCE: 24
MADDQGCIEE QGVEDSANED SVDAKPDRSS FVPSLFSKKK KNVTMRSIKT TRDRVPTYQY     60
NMNFEKLGKC IIINNKNFDK VTGMGVRNGT DKDAEALPKC FRSLGFDVIV YNDCSCAKMQ    120
DLLKKASEED HTNAACFACI LLSHGEENVI YGKDGVTPIK DLTAHFRGDR CKTLLEKPKL    180
FFIQACRGTE LDDGIQADSG PINDTDANPR YKIPVEADFL FAYSTVPGYY SWRSPGRGSW    240
FVQALCSILE EHGKDLEIMQ ILTRVNDRVA RHFESQSDDP HFHEKKQIPC VVSMLTKELY    300
FSQ                                                                303

SEQ ID NO: 25           moltype = AA  length = 479
FEATURE                 Location/Qualifiers
source                  1..479
                        mol_type = protein
                        organism = Homo sapiens
SEQUENCE: 25
```

```
MDFSRNLYDI GEQLDSEDLA SLKFLSLDYI PQRKQEPIKD ALMLFQRLQE KRMLEESNLS   60
FLKELLFRIN RLDLLITYLN TRKEEMEREL QTPGRAQISA YRVMLYQISE EVSRSELRSF  120
KPLLQEEISK CKLDDDMNLL DIFIEMEKRV ILGEGKLDIL KRVCAQINKS LLKIINDYEE  180
FSKERSSSLE GSPDEFSNGE ELCGVMTISD SPREQDSESQ TLDKVYQMKS KPRGYCLIIN  240
NHNFAKAREK VPKLHSIRDR NGTHLDAGAL TTTFEELHFE IKPHDDCTVE QIYEILKIYQ  300
LMDHSNMDCF ICCILSHGDK GIIYGTDGQE APIYELTSQF TGLKCPSLAG KPKVFFIQAC  360
QGDNYQKGIP VETDSEEQPY LEMDLSSPQT RYIPDEADFL LGMATVNNCV SYRNPAEGTW  420
YIQSLCQSLR ERCPRGDDIL TILTEVNYEV SNKDDKKNMG KQMPQPTFTL RKKLVFPSD   479

SEQ ID NO: 26          moltype = AA   length = 416
FEATURE                Location/Qualifiers
source                 1..416
                       mol_type = protein
                       organism = Homo sapiens
SEQUENCE: 26
MDEADRRLLR RCRLRLVEEL QVDQLWDALL SRELFRPHMI EDIQRAGSGS RRDQARQLII   60
DLETRGSQAL PLFISCLEDT GQDMLASFLR TNRQAAKLSK PTLENLTPVV LRPEIRKPEV  120
LRPETPRPVD IGSGGFGDVG ALESLRGNAD LAYILSMEPC GHCLIINNVN FCRESGLRTR  180
TGSNIDCEKL RRRFSSLHFM VEVKGDLTAK KMVLALLELA QQDHGALDCC VVVILSHGCQ  240
ASHLQFPGAV YGTDGCPVSV EKIVNIFNGT SCPSLGGKPK LFFIQACGGE QKDHGFEVAS  300
TSPEDESPGS NPEPDATPFQ EGLRTFDQLD AISSLPTPSD IFVSYSTFPG FVSWRDPKSG  360
SWYVETLDDI FEQWAHSEDL QSLLLRVANA VSVKGIYKQM PGCFNFLRKK LFFKTS      416

SEQ ID NO: 27          moltype = AA   length = 521
FEATURE                Location/Qualifiers
source                 1..521
                       mol_type = protein
                       organism = Homo sapiens
SEQUENCE: 27
MKSQGQHWYS SSDKNCKVSF REKLLIIDSN LGVQDVENLK FLCIGLVPNK KLEKSSSASD   60
VFEHLLAEDL LSEEDPFFLA ELLYIIRQKK LLQHLNCTKE EVERLLPTRQ RVSLFRNLLY  120
ELSEGIDSEN LKDMIFLLKD SLPKTEMTSL SFLAFLEKQG KIDEDNLTCL EDLCKTVVPK  180
LLRNIEKYKR EKAIQIVTPP VDKEAESYQG EEELVSQTDV KTFLEALPQE SWQNKHAGSN  240
GNRATNGAPS LVSRGMQGAS ANTLNSETST KRAAVYRMNR NHRGLCVIVN NHSFTSLKDR  300
QGTHKDAEIL SHVFQWLGFT VHIHNNVTKV EMEMVLQKQK CNPAHADGDC FVFCILTHGR  360
FGAVYSSDEA LIPIREIMSH FTALQCPRLA EKPKLFFIQA CQGEEIQPSV SIEADALNPE  420
QAPTSLQDSI PAEADFLLGL ATVPGYVSFR HVEEGSWYIQ SLCNHLKKLV PRMLKFLEKT  480
MEIRGRKRTV WGAKQISATS LPTAISAQTP RPPMRRWSSV S                     521

SEQ ID NO: 28          moltype = AA   length = 373
FEATURE                Location/Qualifiers
source                 1..373
                       mol_type = protein
                       organism = Homo sapiens
SEQUENCE: 28
MAENKHPDKP LKVLEQLGKE VLTEYLEKLV QSNVLKLKEE DKQKFNNAER SDKRWVFVDA   60
MKKKHSKVGE MLLQTFFSVD PGSHHGEANL EMEEPEESLN TLKLCSPEEF TRLCREKTQE  120
IYPIKEANGR TRKALIICNT EFKHLSLRYG ANFDIIGMKG LLEDLGYDVV VKEELTAEGM  180
ESEMKDFAAL SEHQTSDSTF LVLMSHGTLH GICGTMHSEK TPDVLQYDTI YQIFNNCHCP  240
GLRDKPKVII VQACRGGNSG EMWIRESSKP QLCRGVDLPR NMEADAVKLS HVEKDFIAFY  300
STTPPHHLSYR DKTGGSYFIT RLISCFRKHA CSCHLFDIFL KVQQSFEKAS IHSQMPTIDR  360
ATLTRYFYLF PGN                                                    373

SEQ ID NO: 29          moltype = AA   length = 341
FEATURE                Location/Qualifiers
source                 1..341
                       mol_type = protein
                       organism = Homo sapiens
SEQUENCE: 29
MADEKPSNGV LVHMVKLLIK TFLDGIFDDL MENNVLNTDE IHLIGKCLKF VVSNAENLVD   60
DITETAQTAG KIFREHLWNS KKQLSSDISS DGEREANMPG LNIRNKEFNY LHNRNGSELD  120
LLGMRDLLEN LGYSVVIKEN LTAQEMETAL RQFAAHPEHQ SSDSTFLVFM SHSILNGICG  180
TKHWDQEPDV LHDDTIFEIF NNRCQSLKD KPKVIIMQAC RGNGAGIVWF TTDSGKAGAD  240
THGRLLQGNI CNDAVTKAHV EKDFIAFKSS TPHNVSWRHE TNGSVFISQI IYYFREYSWS  300
HHLEEIFQKV QHSFETPNIL TQLPTIERLS MTRYFYLFPG N                     341

SEQ ID NO: 30          moltype = AA   length = 377
FEATURE                Location/Qualifiers
source                 1..377
                       mol_type = protein
                       organism = Homo sapiens
SEQUENCE: 30
MAEDKHNKNP LKMLESLGKE LISGLLDDFV EKNVLKLEEE EKKKIYDAKL QDKARVLVDS   60
IRQKNQEAGQ VFVQTFLNID KNSTSIKAPE ETVAGPDESV GSAATLKLCP HEEFLKLCKE  120
RAGEIYPIKE RKDRTRLALI ICNTEFDHMP PRNGAALDIL GMKQLLEGLG YTVEVEEKLT  180
ARDMESVLWK FAAREEHKSS DSTFVFMSH GILDGICGTM HSEEEPDVLP YDTIFRTFNN  240
RNCLSLKDKP KVIIVQACRG ANRGELWVSD SPPALADSFS QSSENLEEDA VYKTHVEKDF  300
IAFCSSTPHN VSWRDIKKGS LFITRLITCF QKYAWCCHLE EVFRKVQQSF EKPNVKAQMP  360
TVERLSMTRY FYLFPGN                                                377
```

```
SEQ ID NO: 31              moltype = AA   length = 242
FEATURE                    Location/Qualifiers
source                     1..242
                           mol_type = protein
                           organism = Homo sapiens
SEQUENCE: 31
MSNPRSLEEE KYDMSGARLA LILCVTKARE GSEEDLDALE HMFRQLRFES TMKRDPTAEQ    60
FQEELEKFQQ AIDSREDPVS CAFVVLMAHG REGFLKGEDG EMVKLENLFE ALNNKNCQAL   120
RAKPKVYIIQ ACRGEQRDPG ETVGGDEIVM VIKDSPQTIP TYTDALHVYS TVEGYIAYRH   180
DQKGSCFIQT LVDVFTKRKG HILELLTEVT RRMAEAELVQ EGKARKTNPE IQSTLRKRLY   240
LQ                                                                 242

SEQ ID NO: 32              moltype = AA   length = 480
FEATURE                    Location/Qualifiers
source                     1..480
                           mol_type = protein
                           organism = Homo sapiens
SEQUENCE: 32
MIRAAPPPLF LLLLLLLLLV SWASRGEAAP DQDEIQRLPG LAKQPSFRQY SGYLKGSGSK    60
HLHYWFVESQ KDPENSPVVL WLNGGPGCSS LDGLLTEHGP FLVQPDGVTL EYNPYSWNLI   120
ANVLYLESPA GVGFSYSDDK FYATNDTEVA QSNFEALQPF FRLFPEYKNN KLFLTGESYA   180
GIYIPTLAVL VMQDPSMNLQ GLAVGNGLSS YEQNDNSLVY FAYYHGLLGN RLWSSLQTHC   240
CSQNKCNFYD NKDLECVTNL QEVARIVGNS GLNIYNLYAP CAGGVPSHFR YEKDTVVVQD   300
LGNIFTRLPL KRMWHQALLR SGDKVRMDPP CTNTTAASTY LNNPYVRKAL NIPEQLPQWD   360
MCNFLVNLQY RRLYRSMNSQ YLKLLSSQKY QILLYNGDVD MACNFMGDEW FVDSLNQKME   420
VQRRPWLVKY GDSGEQIAGF VKEFSHIAFL TIKGAGHMVP TDKPLAAFTM FSRFLNKQPY   480

SEQ ID NO: 33              moltype = AA   length = 339
FEATURE                    Location/Qualifiers
source                     1..339
                           mol_type = protein
                           organism = Homo sapiens
SEQUENCE: 33
MWQLWASLCC LLVLANARSR PSFHPLSDEL VNYVNKRNTT WQAGHNFYNV DMSYLKRLCG    60
TFLGGPKPPQ RVMFTEDLKL PASFDAREQW PQCPTIKEIR DQGSCGSCWA FGAVEAISDR   120
ICIHTNAHVS VEVSAEDLLT CCGSMCGDGC NGGYPAEAWN FWTRKGLVSG GLYESHVGCR   180
PYSIPPCEHH VNGSRPPCTG EGDTPKCSKI CEPGYSPTYK QDKHYGYNSY SVSNSEKDIM   240
AEIYKNGPVE GAFSVYSDFL LYKSGVYQHV TGEMMGGHAI RILGWGVENG TPYWLVANSW   300
NTDWGDNGFF KILRGQDHCG IESEVVAGIP RTDQYWEKI                         339

SEQ ID NO: 34              moltype = AA   length = 463
FEATURE                    Location/Qualifiers
source                     1..463
                           mol_type = protein
                           organism = Homo sapiens
SEQUENCE: 34
MGAGPSLLLA ALLLLLSGDG AVRCDTPANC TYLDLLGTWV FQVGSSGSQR DVNCSVMGPQ    60
EKKVVVYLQK LDTAYDDLGN SGHFTIIYNQ GFEIVLNDYK WFAFFKYKEE GSKVTTYCNE   120
TMTGWVHDVL GRNWACFTGK KVGTASENVY VNIAHLKNSQ EKYSNRLYKY DHNFVKAINA   180
IQKSWTATTY MEYETLTLGD MIRRSGGHSR KIPRPKPAPL TAEIQQKILH LPTSWDWRNV   240
HGINFVSPVR NQASCGSCYS FASMGMLEAR IRILTNNSQT PILSPQEVVS CSQYAQGCEG   300
GFPYLIAGKY AQDFGLVEEA CFPYTGTDSP CKMKEDCFRY YSSEYHYVGG FYGGCNEALM   360
KLELVHHGPM AVAFEVYDDF LHYKKGIYHH TGLRDPFNPF ELTNHAVLLV GYGTDSASGM   420
DYWIVKNSWG TGWGENGYFR IRRGTDECAI ESIAVAATPI PKL                    463

SEQ ID NO: 35              moltype = AA   length = 412
FEATURE                    Location/Qualifiers
source                     1..412
                           mol_type = protein
                           organism = Homo sapiens
SEQUENCE: 35
MQPSSLLPLA LCLLAAPASA LVRIPLHKFT SIRRTMSEVG GSVEDLIAKG PVSKYSQAVP    60
AVTEGPIPEV LKNYMDAQYY GEIGIGTPPQ CFTVVFDTGS SNLWVPSIHC KLLDIACWIH   120
HKYNSDKSST YVKNGTSFDI HYGSGSLSGY LSQDTVSVPC QSASSASALG GVKVERQVFG   180
EATKQPGITF IAAKFDGILG MAYPRISVNN VLPVFDNLMQ QKLVDQNIFS FYLSRDPDAQ   240
PGGELMLGGT DSKYYKGSLS YLNVTRKAYW QVHLDQVEVA SGLTLCKEGC EAIVDTGTSL   300
MVGPVDEVRE LQKAIGAVPL IQGEYMIPCE KVSTLPAITL KLGGKGYKLS PEDYTLKVSQ   360
AGKTLCLSGF MGMDIPPPSG PLWILGDVFI GRYYTVFDRN NNRVGFAEAA RL          412

SEQ ID NO: 36              moltype = AA   length = 401
FEATURE                    Location/Qualifiers
source                     1..401
                           mol_type = protein
                           organism = Homo sapiens
SEQUENCE: 36
MKTLLLLLLV LLELGEAQGS LHRVPLRRHP SLKKKLRARS QLSEFWKSHN LDMIQFTESC    60
SMDQSAKEPL INYLDMEYFG TISIGSPPQN FTVIFDTGSS NLWVPSVYCT SPACKTHSRF   120
QPSQSSTYSQ PGQSFSIQYG TGSLSGIIGA DQVSAFATQV EGLTVVGQQF GESVTEPGQT   180
```

```
FVDAEFDGIL GLGYPSLAVG GVTPVFDNMM AQNLVDLPMF SVYMSSNPEG GAGSELIFGG    240
YDHSHFSGSL NWVPVTKQAY WQIALDNIQV GGTVMFCSEG CQAIVDTGTS LITGPSDKIK    300
QLQNAIGAAP VDGEYAVECA NLNVMPDVTF TINGVPYTLS PTAYTLLDFV DGMQFCSSGF    360
QGLDIHPPAG PLWILGDVFI RQFYSVFDRG NNRVGLAPAV P                        401

SEQ ID NO: 37           moltype = AA  length = 484
FEATURE                 Location/Qualifiers
source                  1..484
                        mol_type = protein
                        organism = Homo sapiens
SEQUENCE: 37
MAPWLQLLSL LGLLPGAVAA PAQPRAASFQ AWGPPSPELL APTRFALEMF NRGRAAGTRA     60
VLGLVRGRVR RAGQGSLYSL EATLEEPPCN DPMVCRLPVS KKTLLCSFQV LDELGRHVLL    120
RKDCGPVDTK VPGAGEPKSA FTQGSAMISS LSQNHPDNRN ETFSSVISLL NEDPLSQDLP    180
VKMASIFKNF VITYNRTYES KEEARWRLSV FVNNMVRAQK IQALDRGTAQ YGVTKFSDLT    240
EEEFRTIYLN TLLRKEPGNK MKQAKSVGDL APPEWDWRSK GAVTKVKDQG MCGSCWAFSV    300
TGNVEGQWFL NQGTLLSLSE QELLDCDKMD KACMGGLPSN AYSAIKNLGG LETEDDYSYQ    360
GHMQSCNFSA EKAKVYINDS VELSQNEQKL AAWLAKRGPI SVAINAFGMQ FYRHGISRPL    420
RPLCSPWLID HAVLLVGYGN RSDVPFWAIK NSWGTDWGEK GYYYLHRGSG ACGVNTMASS    480
AVVD                                                                  484

SEQ ID NO: 38           moltype = AA  length = 255
FEATURE                 Location/Qualifiers
source                  1..255
                        mol_type = protein
                        organism = Homo sapiens
SEQUENCE: 38
MQPLLLLLAF LLPTGAEAGE IIGGRESRPH SRPYMAYLQI QSPAGQSRCG GFLVREDFVL     60
TAAHCWGSNI NVTLGAHNIQ RRENTQQHIT ARRAIRHPQY NQRTIQNDIM LLQLSRRVRR    120
NRNVNPVALP RAQEGLRPGT LCTVAGWGRV SMRRGTDTLR EVQLRVQRDR QCLRIFGSYD    180
PRRQICVGDR RERKAAFKGD SGGPLLCNNV AHGIVSYGKS SGVPPEVFTR VSSFLPWIRT    240
TMRSFKLLDQ METPL                                                     255

SEQ ID NO: 39           moltype = AA  length = 335
FEATURE                 Location/Qualifiers
source                  1..335
                        mol_type = protein
                        organism = Homo sapiens
SEQUENCE: 39
MWATLPLLCA GAWLLGVPVC GAAELCVNSL EKFHFKSWMS KHRKTYSTEE YHHRLQTFAS     60
NWRKINAHNN GNHTFKMALN QFSDMSFAEI KHKYLWSEPQ NCSATKSNYL RGTGPYPPSV    120
DWRKKGNFVS PVKNQGACGS CWTFSTTGAL ESAIAIATGK MLSLAEQQLV DCAQDFNNHG    180
CQGGLPSQAF EYILYNKGIM GEDTYPYQGK DGYCKFQPGK AIGFVKDVAN ITIYDEEAMV    240
EAVALYNPVS FAFEVTQDFM MYRTGIYSST SCHKTPDKVN HAVLAVGYGE KNGIPYWIVK    300
NSWGPQWGMN GYFLIERGKN MCGLAACASY PIPLV                               335

SEQ ID NO: 40           moltype = AA  length = 329
FEATURE                 Location/Qualifiers
source                  1..329
                        mol_type = protein
                        organism = Homo sapiens
SEQUENCE: 40
MWGLKVLLLP VVSFALYPEE ILDTHWELWK KTHRKQYNNK VDEISRRLIW EKNLKYISIH     60
NLEASLGVHT YELAMNHLGD MTSEEVVQKM TGLKVPLSHS RSNDTLYIPE WEGRAPDSVD    120
YRKKGYVTPV KNQGQCGSCW AFSSVGALEG QLKKKTGKLL NLSPQNLVDC VSENDGCGGG    180
YMTNAFQYVQ KNRGIDSEDA YPYVGQEESC MYNPTGKAAK CRGYREIPEG NEKALKRAVA    240
RVGPVSVAID ASLTSFQFYS KGVYYDESCN SDNLNHAVLA VGYGIQKGNK HWIIKNSWGE    300
NWGNKGYILM ARNKNNACGI ANLASFPKM                                      329

SEQ ID NO: 41           moltype = AA  length = 333
FEATURE                 Location/Qualifiers
source                  1..333
                        mol_type = protein
                        organism = Homo sapiens
SEQUENCE: 41
MNPTLILAAF CLGIASATLT FDHSLEAQWT KWKAMHNRLY GMNEEGWRRA VWEKNMKMIE     60
LHNQEYREGK HSFTMAMNAF GDMTSEEFRQ VMNGFQNRKP RKGKVFQEPL FYEAPRSVDW    120
REKGYVTPVK NQGQCGSCWA FSATGALEGQ MFRKTGRLIS LSEQNLVDCS QPGQNEGCNG    180
GLMDYAFQYV QDNGGLDSEE SYPYEATEES CKYNPKYSVA NDTGFVDIPK QEKALMKAVA    240
TVGPISVAID AGHESFLFYK EGIYFEPDCS SEDMDHGVLV VGYGFESTES DNNKYWLVKN    300
SWGEEWGMGG YVKMAKDRRN HCGIASAASY PTV                                 333

SEQ ID NO: 42           moltype = AA  length = 334
FEATURE                 Location/Qualifiers
source                  1..334
                        mol_type = protein
                        organism = Homo sapiens
SEQUENCE: 42
MNLSLVLAAF CLGIASAVPK FDQNLDTKWY QWKATHRRLY GANEEGWRRA VWEKNMKMIE     60
```

```
LHNGEYSQGK HGFTMAMNAF GDMTNEEFRQ MMGCFRNQKF RKGKVFREPL FLDLPKSVDW   120
RKKGYVTPVK NQKQCGSCWA FSATGALEGQ MFRKTGKLVS LSEQNLVDCS RPQGNQGCNG   180
GFMARAFQYV KENGGLDSEE SYPYVAVDEI CKYRPENSVA NDTGFTVVAP GKEKALMKAV   240
ATVGPISVAM DAGHSSFQFY KSGIYFEPDC SSKNLDHGVL VVGYGFEGAN SNNSKYWLVK   300
NSWGPEWGSN GYVKIAKDKN NHCGIATAAS YPNV                              334

SEQ ID NO: 43           moltype = AA  length = 321
FEATURE                 Location/Qualifiers
source                  1..321
                        mol_type = protein
                        organism = Homo sapiens
SEQUENCE: 43
MDVRALPWLP WLLWLLCRGG GDADSRAPFT PTWPRSRERE AAAFRESLNR HRYLNSLFPS    60
ENSTAFYGIN QFSYLFPEEF KAIYLRSKPS KFPRYSAEVH MSIPNVSLPL RFDWRDKQVV   120
TQVRNQQMCG GCWAFSVVGA VESAYAIKGK PLEDLSVQQV IDCSYNNYGC NGGSTLNALN   180
WLNKMQVKLV KDSEYPFKAQ NGLCHYFSGS HSGFSIKGYS AYDFSDQEDE MAKALLTFGP   240
LVVIVDAVSW QDYLGGIIQH HCSSGEANHA VLITGFDKTG STPYWIVRNS WGSSWGVDGY   300
AHVKMGSNVC GIADSVSSIF V                                            321

SEQ ID NO: 44           moltype = AA  length = 331
FEATURE                 Location/Qualifiers
source                  1..331
                        mol_type = protein
                        organism = Homo sapiens
SEQUENCE: 44
MKRLVCVLLV CSSAVAQLHK DPTLDHHWHL WKKTYGKQYK EKNEEAVRRL IWEKNLKFVM    60
LHNLEHSMGM HSYDLGMNHL GDMTSEEVMS LMSSLRVPSQ WQRNITYKSN PNRILPDSVD   120
WREKGCVTEV KYQGSCGACW AFSAVGALEA QLKLKTGKLV SLSAQNLVDC STEKYGNKGC   180
NGGFMTTAFQ YIIDNKGIDS DASYPYKAMD QKCQYDSKYR AATCSKYTEL PYGREDVLKE   240
AVANKGPVSV GVDARHPSFF LYRSGVYYEP SCTQNVNHGV LVVGYGDLNG KEYWLVKNSW   300
GHNFGEEGYI RMARNKGNHC GIASFPSYPE I                                 331

SEQ ID NO: 45           moltype = AA  length = 376
FEATURE                 Location/Qualifiers
source                  1..376
                        mol_type = protein
                        organism = Homo sapiens
SEQUENCE: 45
MALTAHPSCL LALLVAGLAQ GIRGPLRAQD LGPQPLELKE AFKLFQIQFN RSYLSPEEHA    60
HRLDIFAHNL AQAQRLQEED LGTAEFGVTP FSDLTEEEFG QLYGYRRAAG GVPSMGREIR   120
SEEPEESVPF SCDWRKVASA ISPIKDQKNC NCCWAMAAAG NIETLWRISF WDFVDVSVQE   180
LLDCGRCGDG CHGGFVWDAF ITVLNNSGLA SEKDYPFQGK VRAHRCHPKK YQKVAWIQDF   240
IMLQNNEHRI AQYLATYGPI TVTINMKPLQ LYRKGVIKAT PTTCDPQLVD HSVLLVGFGS   300
VKSEEGIWAE TVSSQSQPQP PHPTPYWILK NSWGAQWGEK GYFRLHRGSN TCGITKFPLT   360
ARVQKPDMKP RVSCPP                                                  376

SEQ ID NO: 46           moltype = AA  length = 303
FEATURE                 Location/Qualifiers
source                  1..303
                        mol_type = protein
                        organism = Homo sapiens
SEQUENCE: 46
MARRGPGWRP LLLLVLLAGA AQGGLYFRRG QTCYRPLRGD GLAPLGRSTY PRPHEYLSPA    60
DLPKSWDWRN VDGVNYASIT RNQHIPQYCG SCWAHASTSA MADRINIKRK GAWPSTLLSV   120
QNVIDCGNAG SCEGGNDLSV WDYAHQHGIP DETCNNYQAH DQECDKFNQC GTCNEFKECH   180
AIRNYTLWRV GDYGSLSGRE KMMAEIYANG PISCGIMATE RLANYTGGIY AEYQDTTYIN   240
HVVSVAGWGI SDGTEYWIVR NSWGEPWGER GWLRIVTSTY KDGKGARYNL AIEEHCTFGD   300
PIV                                                                303

SEQ ID NO: 47           moltype = AA  length = 338
FEATURE                 Location/Qualifiers
source                  1..338
                        mol_type = protein
                        organism = Homo sapiens
SEQUENCE: 47
MLQKPKSVKL RALRSPRKFG VAGRSCQEVL RKGCLRFQLP ERGSRLCLYE DGTELTEDYF    60
PSVPDNAELV LLTLGQAWQG YVSDIRRFLS AFHEPQVGLI QAAQQLLCDE QAPQRQRLLA   120
DLLHNVSQNI AAETRAEDPP WFEGLESRFQ SKSGYLRYSC ESRIRSYLRE VSSYPSTVGA   180
EAQEEFLRVL GSMCQRLRSM QYNGSYFDRG AKGGSRLCTP EGWFSCGPF DMDSCLSRHS   240
INPYSNRESR ILFSTWNLDH IIEKKRTIIP TLVEAIKEQD GREVDWEYFY GLLFTSENLK   300
LVHIVCHKKT THKLNCDPSR IYKPQTRLKR KQPVRKRQ                          338

SEQ ID NO: 48           moltype = AA  length = 360
FEATURE                 Location/Qualifiers
source                  1..360
                        mol_type = protein
                        organism = Homo sapiens
SEQUENCE: 48
MSQERPTFYR QELNKTIWEV PERYQNLSPV GSGAYGSVCA AFDTKTGLRV AVKKLSRPFQ    60
```

```
SIIHAKRTYR ELRLLKHMKH ENVIGLLDVF TPARSLEEFN DVYLVTHLMG ADLNNIVKCQ    120
KLTDDHVQFL IYQILRGLKY IHSADIIHRD LKPSNLAVNE DCELKILDFG LARHTDDEMT    180
GYVATRWYRA PEIMLNWMHY NQTVDIWSVG CIMAELLTGR TLFPGTDHID QLKLILRLVG    240
TPGAELLKKI SSESARNYIQ SLTQMPKMNF ANVFIGANPL AVDLLEKMLV LDSDKRITAA    300
QALAHAYFAQ YHDPDDEPVA DPYDQSFESR DLLIDEWKSL TYDEVISFVP PPLDQEEMES    360

SEQ ID NO: 49          moltype = AA   length = 364
FEATURE                Location/Qualifiers
source                 1..364
                       mol_type = protein
                       organism = Homo sapiens
SEQUENCE: 49
MSGPRAGFYR QELNKTVWEV PQRLQGLRPV GSGAYGSVCS AYDARLRQKV AVKKLSRPFQ     60
SLIHARRTYR ELRLLKHLKH ENVIGLLDVF TPATSIEDFS EVYLVTTLMG ADLNNIVKCQ    120
ALSDEHVQFL VYQLLRGLKY IHSAGIIHRD LKPSNVAVNE DCELRILDFG LARQADEEMT    180
GYVATRWYRA PEIMLNWMHY NQTVDIWSVG CIMAELLQGK ALFPGSDYID QLKRIMEVVG    240
TPSPEVLAKI SSEHARTYIQ SLPPMPQKDL SSIFRGANPL AIDLLGRMLV LDSDQRVSAA    300
EALAHAYFSQ YHDPEDEPEA EPYDESVEAK ERTLEEWKEL TYQEVLSFKP PEPPKPPGSL    360
EIEQ                                                                364

SEQ ID NO: 50          moltype = AA   length = 367
FEATURE                Location/Qualifiers
source                 1..367
                       mol_type = protein
                       organism = Homo sapiens
SEQUENCE: 50
MSSPPPARSG FYRQEVTKTA WEVRAVYRDL QPVGSGAYGA VCSAVDGRTG AKVAIKKLYR     60
PFQSELFAKR AYRELRLLKH MRHENVIGLL DVFTPDETLD DFTDFYLVMP FMGTDLGKLM    120
KHEKLGEDRI QFLVYQMLKG LRYIHAAGII HRDLKPGNLA VNEDCELKIL DFGLARQADS    180
EMTGYVVTRW YRAPEVILNW MRYTQTVDIW SVGCIMAEMI TGKTLFKGSD HLDQLKEIMK    240
VTGTPPAEFV QRLQSDEAKN YMKGLPELEK KDFASILTNA SPLAVNLLEK MLVLDAEQRV    300
TAGEALAHPY FESLHDTEDE PQVQKYDDSF DDVDRTLDEW KRVTYKEVLS FKPPRQLGAR    360
VSKETPL                                                             367

SEQ ID NO: 51          moltype = AA   length = 365
FEATURE                Location/Qualifiers
source                 1..365
                       mol_type = protein
                       organism = Homo sapiens
SEQUENCE: 51
MSLIRKKGFY KQDVNKTAWE LPKTYVSPTH VGSGAYGSVC SAIDKRSGEK VAIKKLSRPF     60
QSEIFAKRAY RELLLLKHMQ HENVIGLLDV FTPASSLRNF YDFYLVMPFM QTDLQKIMGM    120
EFSEEKIQYL VYQMLKGLKY IHSAGVVHRD LKPGNLAVNE DCELKILDFG LARHADAEMT    180
GYVVTRWYRA PEVILSWMHY NQTVDIWSVG CIMAEMLTGK TLFKGKDYLD QLTQILKVTG    240
VPGTEFVQKL NDKAAKSYIQ SLPQTPRKDF TQLFPPRASPQ AADLLEKMLE LDVDKRLTAA   300
QALTHPFFEP FRDPEEETEA QQPFDDSLEH EKLTVDEWKQ HIYKEIVNFS PIARKDSRRR    360
SGMKL                                                               365

SEQ ID NO: 52          moltype = AA   length = 403
FEATURE                Location/Qualifiers
source                 1..403
                       mol_type = protein
                       organism = Homo sapiens
SEQUENCE: 52
MTAIIKEIVS RNKRRYQEDG FDLDLTYIYP NIIAMGFPAE RLEGVYRNNI DDVVRFLDSK     60
HKNHYKIYNL CAERHYDTAK FNCRVAQYPF EDHNPPQLEL IKPFCEDLDQ WLSEDDNHVA    120
AIHCKAGKGR TGVMICAYLL HRGKFLKAQE ALDFYGEVRT RDKKGVTIPS QRRYVYYYSY    180
LLKNHLDYRP VALLFHKMMF ETIPMFSGGT CNPQFVVCQL KVKIYSSNSG PTRREDKFMY    240
FEFPQPLPVC GDIKVEFFHK QNKMLKKDKM FHFWVNTFPI PGPEETSEKV ENGSLCDQEI    300
DSICSIERAD NDKEYLVLTL TKNDLDKANK DKANRYFSPN FKVKLYFTKT VEEPSNPEAS    360
SSTSVTPDVS DNEPDHYRYS DTTDSDPENE PFDEDQHTQI TKV                      403

SEQ ID NO: 53          moltype = AA   length = 1154
FEATURE                Location/Qualifiers
source                 1..1154
                       mol_type = protein
                       organism = Homo sapiens
SEQUENCE: 53
MQYLNIKEDC NAMAFCAKMR SSKKTEVNLE APEPGVEVIF YLSDREPLRL GSGEYTAEEL     60
CIRAAQACRI SPLCHNLFAL YDENTKLWYA PNRTITVDDK MSLRLHYRMR FYFTNWHGTN    120
DNEQSVWRHS PKKQNGYEK  KKIPDATPLL DASSLEYLFA QGQYDLVKCL APIRDPKTEQ    180
DGHDIENECL GMAVLAISHY AMMKKMQLPE LPKDISYKRY IPETLNKSIR QRNLLTRMRI    240
NNVFKDFLKE FNNKTICDSS VSTHDLKVKY LATLETLTKH YGAEIFETSM LLISSENEMN    300
WFHSNDGGNV LYYEMVMTGN LGIQWRHKPN VVSVEKEKNK LKRKKLENKH KKDEEKNKIR    360
EEWNNFSYFP EITHIVIKES VVSINKQDNK KMELKLSSHE EALSFVSLVD GYFRLTADAH    420
HYLCTDVAPP LIVHNIQNGC HGPICTEYAI NKLRQEGSEE GMYVLRWSCT DFDNILMTVT    480
CFEKSEQVQG AQKQFKNFQI EVQKGRYSLH GSDRSFPSLG DLMSHLKKQI LRTDNISFML    540
KRCCQPKPRE ISNLLVATKK AQEWQPVYPM SQLSFDRILK KDLVQGEHLG RGTRTHIYSG    600
TLMDYKDDEG TSEEKKIKVI LKVLDPSHRD ISLAFFEAAS MMRQVSHKHI VYLYGVCVRD    660
```

```
VENIMVEEFV EGGPLDLFMH RKSDVLTTPW KFKVAKQLAS ALSYLEDKDL VHGNVCTKNL   720
LLAREGIDSE CGPFIKLSDP GIPITVLSRQ ECIERIPWIA PECVEDSKNL SVAADKWSFG   780
TTLWEICYNG EIPLKDKTLI EKERFYESRC RPVTPSCKEL ADLMTRCMNY DPNQRPFFRA   840
IMRDINKLEE QNPDIVSEKK PATEVDPTHF EKRFLKRIRD LGEGHFGKVE LCRYDPEGDN   900
TGEQVAVKSL KPESGGNHIA DLKKEIEILR NLYHENIVKY KGICTEDGGN GIKLIMEFLP   960
SGSLKEYLPK NKNKINLKQQ LKYAVQICKG MDYLGSRQYV HRDLAARNVL VESEHQVKIG  1020
DFGLTKAIET DKEYYTVKDD RDSPVFWYAP ECLMQSKFYI ASDVWSFGVT LHELLTYCDS  1080
DSSPMALFLK MIGPTHGQMT VTRLVNTLKE GKRLPCPPNC PDEVYQLMRK CWEFQPSNRT  1140
SFQNLIEGFE ALLK                                                   1154

SEQ ID NO: 54           moltype = AA  length = 1132
FEATURE                 Location/Qualifiers
source                  1..1132
                        mol_type = protein
                        organism = Homo sapiens
SEQUENCE: 54
MGMACLTMTE MEGTSSSIY QNGDISGNAN SMKQIDPVLQ VYLYHSLGKS EADYLTFPSG    60
EYVAEEICIA ASKACGITPV YHNMFALMSE TERIWYPPNH VFHIDESTRH NVLYIRIFYF   120
PRWYCSGSNR AYRHGISRGA EAPLLDDFVM SYLFAQWRHD FVHGWIKVPV THETQEECLG   180
MAVLDMMRIA KENDQTPLAI YNSISYKTFL PKCIRAKIQD YHILTRKRIR YRFRRFIQQF   240
SQCKATARNL KLKYLINLET LQSAFYTEKF EVKEPGSGPS GEEIFATIII TGNGGIQWSR   300
GKHKESETLT EQDLQLYCDF PNIIDVSIKQ ANQEGSNESR VVTIHKQDGK NLEIELSLSR   360
EALSFVSLID GYYRLTADAH HYLCKEVAPP AVLENIQSNC HGPISMDFAI SKLKKAGNQT   420
GLYVLRCSPK DFNKYFLTFA VERENVIEYK HCLITKNENE EYNLSGTKKN FSSLKDLLNC   480
YQMETVRSDN IIFQFTKCCP PKPKDKSNLL VFRTNGVSDV PTSPTLQRPT HMNQMVFHKI   540
RNEDLIFNES LGQGTFTKIF KGVRREVGDY GQLHETEVLL KVLDKAHRNY SESFFEAASM   600
MSKLSHKHLV LNYGVCVCGD ENILVQEFVK FGSLDTYLKK NKNCINILWK LEVAKQLAWA   660
MHFLEENTLI HGNVCAKNIL LIREEDRKTG NPPFIKLSDP GISITVLPKD ILQERIPWVP   720
PECIENPKNL NLATDKWSFG TTLWEICSGG DKPLSALDSQ RKLQFYEDRH QLPAPKWAEL   780
ANLINNCMDY EPDFRPSFRA IIRDLNSLFT PDYELLTEND MLPNMRIGAL GPSGAFEDRD   840
PTQFEERHLK FLQQLGKGNF GSVEMCRYDP LQDNTGEVVA VKKLQHSTEE HLRDFEREIE   900
ILKSLQHDNI VKYKGVCYSA GRRNLKLIME YLPYGSLRDY LQKHKERIDH IKLLQYTSQI   960
CKGMEYLGTK RYIHRDLATR NILVENENRV KIGDFGLTKV LPQDKEYYKV KEPGESPIFW  1020
YAPESLTESK FSVASDVWSF GVVLYELFTY IEKSKSPPAE FMRMIGNDKQ GQMIVFHLIE  1080
LLKNNGRLPR PDGCPDEIYM IMTECWNNNV NQRPSFRDLA LRVDQIRDNM AG         1132

SEQ ID NO: 55           moltype = AA  length = 1124
FEATURE                 Location/Qualifiers
source                  1..1124
                        mol_type = protein
                        organism = Homo sapiens
SEQUENCE: 55
MAPPSEETPL IPQRSCSLLS TEAGALHVLL PARGPGPPQR LSFSFGDHLA EDLCVQAAKA    60
SGILPVYHSL FALATEDLSC WFPPSHIFSV EDASTQVLLY RIRFYFPNWF GLEKCHRFGL   120
RKDLASAILD LPVLEHLFAQ HRSDLVSGRL PVGLSLKEQG ECLSLAVLDL ARMAREQAQR   180
PGELLKTVSY KACLPPSLRD LIQGLSFVTR RRIRRTVRRA LRRVAACQAD RHSLMAKYIM   240
DLERLDPAGA AETFHVGLPG ALGGHDGLGL LRVAGDGGLA WTQGEQEVLQ PPFCDFPEIVD   300
ISIKQAPRVG PAGEHRLVTV TRTDNQILEA EFPGLPEALS FVALVDGYFR LTTDSQHFFC   360
KEVAPPRLLE EVAEQCHGPI TLDFAINKLK TGGSRPGSYV LRRSPQDFDS FLLTVCVQNP   420
LGPDYKGCLI RRSPTGTFLL VGLSRPHSSL RELLATCWDG GLHVDGVAVT LTSCCIPRPK   480
EKSNLIVVQR GHSPPTSSLV QPQSQYQLSQ MTFHKIPADS LEWHENLGHG SFTKIYRGCR   540
HEVVDGEARK TEVLLKVMDA KHKNCMESFL EAASLMSQVS YRHLVLLHGV CMAGDSTMVQ   600
EFVHLGAIDM YLRKRGHLVP ASWKLQVVKQ LAYALNYLED KGLPHGNVSA RKVLLAREGA   660
DGSPPFIKLS DPGVSPAVLS LEMLTDRIPW VAPECLREAQ TLSLEADKWG FGATVWEVFS   720
GVTMPISALD PAKKLQFYED RQQLPAPKWT ELALLIQQCM AYEPVQRPSF RAVIRDLNSL   780
ISSDYELLSD PTPGALAPRD GLWNGAQLYA CQDPTIFEER HLKYISQLGK GNFGSVELCR   840
YDPLGDNTGA LVAVKQLQHS GPDQQRDFQR EIQILKALHS DFIVKYRGVS YGPGRQSLRL   900
VMEYLPSGCL RDFLQRHRAR LDASRLLLYS SQICKGMEYL GSRRCVHRDL AARNILVESE   960
AHVKIADFGL AKLLPDKDY  YVVREPGQSP IFWYAPESLS DNIFSRQSDV WSFGVVLYEL  1020
FTYCDKSCSP SAEFLRMMGC ERDVPALCRL LELLEEGQRL PAPPACPAEV HELMKLCWAP  1080
SPQDRPSFSA LGPQLDMLWS GSRGCETHAF TAHPEGKHHS LSFS                  1124

SEQ ID NO: 56           moltype = AA  length = 1187
FEATURE                 Location/Qualifiers
source                  1..1187
                        mol_type = protein
                        organism = Homo sapiens
SEQUENCE: 56
MPLRHWGMAR GSKPVGDGAQ PMAAMGGLKV LLHWAGPGGG EPWVTFSESS LTAEEVCIHI    60
AHKVGITPPC FNLFALFDAQ AQVWLPPNHI LEIPRDASLM LYFRIRFYFR NWHGMNPREP   120
AVYRCGPPGT EASSDQTAQG MQLLDPASFE YLFEQGKHEF VNDVASLWEL STEEEIHHFK   180
NESLGMAFLH LCHLALRHGI PLEEVAKKTS FKDCIPRSFR RHIRQHSALT RLRLRNVFRR   240
FLRDFQPGRL SQQMVMVKYL ATLERLAPRF GTERVPVCHL RLLAQAEGEP CYIRDSGVAP   300
TDPGPESAAG PPTHEVLVTG TGGIQWWPVE EEVNKEEGSS GSSGRNPQAS LFGKKAKAHK   360
AVGQPADRPR EPLWAYFCDF RDITHVVLKE HCVSIHRQDN KCLELSLPSR AAALSFVSLV   420
DGYFRLTADS SHYLCHEVAP PRLVMSIRDG IHGPLLEPPV QAKLRPEDGL YLIHWSTSHP   480
YRLILTVAQR SQAPDGMQSL RLRKFPIEQQ DGAFVLEGWG RSFPSVRELG AALQGCLLRA   540
GDDCFSLRRC CLPQPGETSN LIIMRGARAS PRTLNLSQLS FHRVDQKEIT QLSHLGQGTR   600
TNVYEGRLRV EGSGDPEEGK MDDEDPLVPG RDRGQELRVV LKVVLDPSHHD IALAFYETAS   660
```

```
LMSQVSHTHL AFVHGVCVRG PENIMVTEYV EHGPLDVWLR RERGHVPMAW KMVVAQQLAS    720
ALSYLENKNL VHGNVCGRNI LLARLGLAEG TSPFIKLSDP GVGLGALSRE ERVERIPWLA    780
PECLPGGANS LSTAMDKWGF GATLLEICFD GEAPLQSRSP SEKEHFYQRQ HRLPEPSCPQ    840
LATLTSQCLT YEPTQRPSFR TILRDLTRLQ PHNLADVLTV NPDSPASDPT VFHKRYLKKI    900
RDLGEGHFGK VSLYCYDPTN DGTGEMVAVK ALKADCGPQH RSGWKQEIDI LRTLYHEHII    960
KYKGCCEDQG EKSLQLVMEY VPLGSLRDYL PRHSIGLAQL LLFAQQICEG MAYLHAQHYI   1020
HRDLAARNVL LDNDRLVKIG DFGLAKAVPE GHEYYRVRED GDSPVFWYAP ECLKEYKFYY   1080
ASDVWSFGVT LYELLTHCDS SQSPPTKFLE LIGIAQGQMT VLRLTELLER GERLPRPDKC   1140
PCEVYHLMKN CWETEASFRP TFENLIPILK TVHEKYQGQA PSVFSVC                 1187

SEQ ID NO: 57           moltype = AA   length = 906
FEATURE                 Location/Qualifiers
source                  1..906
                        mol_type = protein
                        organism = Homo sapiens
SEQUENCE: 57
MAGNVKKSSG AGGGSGSGGS GSGGLIGLMK DAFQPHHHHH HHLSPHPPGT VDKKMVEKCW     60
KLMDKVVRLC QNPKLALKNS PPYILDLLPD TYQHLRTILS RYEGKMETLG ENEYFRVFME    120
NLMKKTKQTI SLFKEGKERM YEENSQPRRN LTKLSLIFSH MLAELKGIFP SGLFQGDTFR    180
ITKADAAEFW RKAFGEKTIV PWKSFRQALH EVHPISSGLE AMALKSTIDL TCNDYISVFE    240
FDIFTRLFQP WSSLLRNWNS LAVTHPGYMA FLTYDEVKAR LQKFIHKPGS YIFRLSCTRL    300
GQWAIGYVTA DGNILQTIPH NKPLFQALID GFREGFYLFP DGRNQNPDLT GLCEPTPQDH    360
IKVTQEQYEL YCEMGSTFQL CKICAENDKD VKIEPCGHLM CTSCLTSWQE SEGQGCPFCR    420
CEIKGTEPIV VDPFDPRGSG SLLRQGAEGA PSPNYDDDDD ERADDTLFMM KELAGAKVER    480
PPSPFSMAPQ ASLPPVPPRL DLLPQRVCVP SSASALGTAS KAASGSLHKD KPLPVPPTLR    540
DLPPPPPPDR PYSVGAESRP QRRPLPCTPG DCPSRDKLPP VPSSRLGDSW LPRPIPKVPV    600
SAPSSSDPWT GRELTNRHSL PFSLPSQMEP RPDVPRLGST FSLDTSMSMN SSPLVGPECD    660
HPKIKPSSSA NAIYSLAARP LPVPKLPPGE QCEGEEDTEY MTPSSRPLRP LDTSQSSRAC    720
DCDQQQIDSCT YEAMYNIQSQ APSITESSTF GEGNLAAAHA NTGPEESENE DDGYDVPKPP   780
VPAVLARRTL SDISNASSSF GWLSLDGDPT TNVTEGSQVP ERPPKPFPRR INSERKAGSC    840
QQGSGPAASA ATASPQLSSE IENLMSQGYS YQDIQKALVI AQNNIEMAKN ILREFVSISS    900
PAHVAT                                                               906

SEQ ID NO: 58           moltype = AA   length = 465
FEATURE                 Location/Qualifiers
source                  1..465
                        mol_type = protein
                        organism = Homo sapiens
SEQUENCE: 58
MIVFVRFNSS HGFPVEVDSD TSIFQLKEVV AKRQGVPADQ LRVIFAGKEL RNDWTVQNCD     60
LDQQSIVHIV QRPWRKGQEM NATGGDDPRN AAGGCEREPQ SLTRVDLSSS VLPGDSVGLA    120
VILHTDSRKD SPPAGSPAGR SIYNSFYVYC KGPCQRVQPG KLRVQCSTCR QATLTLTQGP    180
SCWDDVLIPN RMSGECQSPH CPGTSAEFFF KCGAHPTSDL ETSVALHLIA TNSRNITCIT    240
CTDVRSPVLV FQCNSRHVIC LDCFHLYCVT RLNDRQFVHD PQLGYSLPCV AGCPNSLIKE    300
LHHFRILGEE QYNRYQQYGA EECVLQMGGV LCPRPGCGAG LLPEPDQRKV TCEGGNGLGC    360
GFAFCRECKE AYHEGECSAV FEASGTTTQA YRVDERAAEQ ARWEAASKET IKKTTKPCPR    420
CHVPVEKNGG CMHMKCPQPQ CRLEWCWNCG CEWNRVCMGD HWFDV                    465

SEQ ID NO: 59           moltype = AA   length = 108
FEATURE                 Location/Qualifiers
source                  1..108
                        mol_type = protein
                        organism = Homo sapiens
SEQUENCE: 59
MAAAMDVDTP SGTNSGAGKK RFEVKKWNAV ALWAWDIVVD NCAICRNHIM DLCIECQANQ     60
ASATSEECTV AWGVCNHAFH FHCISRWLKT RQVCPLDNRE WEFQKYGH                 108

SEQ ID NO: 60           moltype = AA   length = 501
FEATURE                 Location/Qualifiers
source                  1..501
                        mol_type = protein
                        organism = Homo sapiens
SEQUENCE: 60
MAAASVTPPG SLELLQPGFS KTLLGTKLEA KYLCSACRNV LRRPFQAQCG HRYCSFCLAS     60
ILSSGPQNCA ACVHEGIYEE GISILESSSA FPDNAARREV ESLPAVCPSD GCTWKGTLKE    120
YESCHEGRCP LMLTECPACK GLVRLGEKER HLEHECPERS LSCRHCRAPC CGADVKAHHE    180
VCPKFPLTCD GCGKKKIPRE KFQDHVKTCG KCRVPCRFHA IGCLETVEGE KQQEHEVQWL    240
REHLAMLLSS VLEAKPLLGD QSHAGSELLQ RCESLEKKTA TFENIVCVLN REVERVAMTA    300
EACSRQHRLD QDKIEALSSK VQQLERSIGL KDLAMADLEQ KVLEMEASTY DGVFIWKISD    360
FARKRQEAVA GRIPAIFSPA FYTSRYGYKM CLRIYLNGDG TGRGTHLSLF FVVMKGPNDA    420
LLRWPFNQKV TLMLLDQNNR EHVIDAFRPV VTSSSFQRPV NDMNIASGCP LFCPVSKMEA    480
KNSYVRDDAI FIKAIVDLTG L                                              501

SEQ ID NO: 61           moltype = AA   length = 491
FEATURE                 Location/Qualifiers
source                  1..491
                        mol_type = protein
                        organism = Homo sapiens
SEQUENCE: 61
```

```
MCNTNMSVPT DGAVTTSQIP ASEQETLVRP KPLLLKLLKS VGAQKDTYTM KEVLFYLGQY    60
IMTKRLYDEK QQHIVYCSND LLGDLFGVPS FSVKEHRKIY TMIYRNLVVV NQQESSDSGT   120
SVSENRCHLE GGSDQKDLVQ ELQEEKPSSS HLVSRPSTSS RRRAISETEE NSDELSGERQ   180
RKRHKSDSIS LSFDESLALC VIREICCERS SSSESTGTPS NPDLDAGVSE HSGDWLDQDS   240
VSDQFSVEFE VESLDSEDYS LSEEGQELSD EDDEVYQVTV YQAGESDTDS FEEDPEISLA   300
DYWKCTSCNE MNPPLPSHCN RCWALRENWL PEDKGKDKGE ISEKAKLENS TQAEEGFDVP   360
DCKKTIVNDS RESCVEENDD KITQASQSQE SEDYSQPSTS SSIIYSSQED VKEFEREETQ   420
DKEESVESSL PLNAIEPCVI CQGRPKNGCI VHGKTGHLMA CFTCAKKLKK RNKPCPVCRQ   480
PIQMIVLTYF P                                                       491

SEQ ID NO: 62           moltype = AA  length = 240
FEATURE                 Location/Qualifiers
source                  1..240
                        mol_type = protein
                        organism = Renilla reniformis
SEQUENCE: 62
MTSKVYDPEQ RKRMITGPQW WARCKQMNVL DSFINYYDSE KHAENAVIFL HGNAASSYLW    60
RHVVPHIEPV ARCIIPDLIG MGKSGKSGNG SYRLLDHYKY LTAWFELLNL PKKIIFVGHD   120
WGACLAFHYS YEHQDKIKAI VHAESVVDVI ESWDEWPDIE EDIALIKSEE GEKMVLENNF   180
FVETMLPSKI MRKLEPEEFA AYLEPFKEKG EVRRPTLSWP REIPLVKGGK PDVVQIVRNY   240

SEQ ID NO: 63           moltype = AA  length = 320
FEATURE                 Location/Qualifiers
source                  1..320
                        mol_type = protein
                        organism = Homo sapiens
SEQUENCE: 63
MELLSPPLRD VDLTAPDGSL CSFATTDDFY DDPCFDSPDL RFFEDLDPRL MHVGALLKPE    60
EHSHFPAAVH PAPGAREDEH VRAPSGHHQA GRCLLWACKA CKRKTTNADR RKAATMRERR   120
RLSKVNEAFE TLKRCTSSNP NQRLPKVEIL RNAIRYIEGL QALLRDQDAA PPGAAAAFYA   180
PGPLPPGRGG EHYSGDSDAS SPRSNCSDGM MDYSGPPSGA RRRNCYEGAY YNEAPSEPRP   240
GKSAAVSSLD CLSSIVERIS TESPAAPALL LADVPSESPP RRQEAAAPSE GESSGDPTQS   300
PDAAPQCPAG ANPNPIYQVL                                              320

SEQ ID NO: 64           moltype = AA  length = 607
FEATURE                 Location/Qualifiers
source                  1..607
                        mol_type = protein
                        organism = Homo sapiens
SEQUENCE: 64
MAEKRRGSPC SMLSLKAHAF SVEALIGAEK QQQLQKKRRK LGAEEEAAGAV DDGGCSRGGG   60
AGEKGSSEGD EGAALPPPAG ATSGPARSGA DLERGAAGGC EDGFQQGASP LASPGGSPKG   120
SPARSLARPG TPLPSPQAPR VDLQGAELWK RFHEIGTEMI ITKAGRRMFP AMRVKISGLD   180
PHQQYYIAMD IVPVDNKRYR YVYHSSKWMV AGNADSPVPP RVYIHPDSPA SGETWMRQVI   240
SFDKLKLTNN ELDDQGHIIL HSMHKYQPRV HVIRKDCGDD LSPIKPVPSG EGVKAFSFPE   300
TVFTTVTAYQ NQQITRLKID RNPFAKGFRD SGRNRMGLEA LVESYAFWRP SLRTLTFEDI   360
PGIPKQGNAS SSTLLQGTGN GVPATHPHLL SGSSCSSPAF HLGPNTSQLC SLAPADYSAC   420
ARSGLTLNRY STSLAETYNR LTNQAGETFA PPRTPSYVGV SSSTSVNMSM GGTDGDTFSC   480
PQTSLSMQIS GMSPQLQYIM PSPSSNAFAT NQTHQGSYNT FRLHSPCALY GYNFSTSPKL   540
AASPEKIVSS QGSFLGSSPS GTMTDRQMLP PVEGVHLLSS GGQQSFFDSR TLGSLTLSSS   600
QVSAHMV                                                            607

SEQ ID NO: 65           moltype = AA  length = 393
FEATURE                 Location/Qualifiers
source                  1..393
                        mol_type = protein
                        organism = Homo sapiens
SEQUENCE: 65
MEEPQSDPSV EPPLSQETFS DLWKLLPENN VLSPLPSQAM DDLMLSPDDI EQWFTEDPGP    60
DEAPRMPEAA PPVAPAPAAP TPAAPAPAPS WPLSSSVPSQ KTYQGSYGFR LGFLHSGTAK   120
SVTCTYSPAL NKMFCQLAKT CPVQLWVDST PPPGTRVRAM AIYKQSQHMT EVVRRCPHHE   180
RCSDSDGLAP PQHLIRVEGN LRVEYLDDRN TFRHSVVVPY EPPEVGSDCT TIHYNYMCNS   240
SCMGGMNRRP ILTIITLEDS SGNLLGRNSF EVRVCACPGR DRRTEEENLR KKGEPHHELP   300
PGSTKRALPN NTSSSPQPKK KPLDGEYFTL QIRGRERFEM FRELNEALEL KDAQAGKEPG   360
GSRAHSSHLK SKKGQSTSRH KKLMFKTEGP DSD                                393

SEQ ID NO: 66           moltype = AA  length = 215
FEATURE                 Location/Qualifiers
source                  1..215
                        mol_type = protein
                        organism = Homo sapiens
SEQUENCE: 66
MGKGDPKKPR GKMSSYAFFV QTCREEHKKK HPDASVNFSE FSKKCSERWK TMSAKEKGKF    60
EDMAKADKAR YEREMKTYIP PKGETKKKFK DPNAPKRPPS AFFLFCSEYR PKIKGEHPGL   120
SIGDVAKKLG EMWNNTAADD KQPYEKKAAK LKEKYEKDIA AYRAKGKPDA AKKGVVKAEK   180
SKKKKEEEED EDEEDEEEE EDEEDEDEEE DDDDE                              215

SEQ ID NO: 67           moltype = AA  length = 356
FEATURE                 Location/Qualifiers
```

```
source                          1..356
                                mol_type = protein
                                organism = Homo sapiens
SEQUENCE: 67
MTKSYSESGL MGEPQPQGPP SWTDECLSSQ DEEHEADKKE DDLETMNAEE DSLRNGGEEE    60
DEDEDLEEEE EEEEEDDDQK PKRRGPKKKK MTKARLERFK LRRMKANARE RNRMHGLNAA   120
LDNLRKVVPC YSKTQKLSKI ETLRLAKNYI WALSEILRSG KSPDLVSFVQ TLCKGLSQPT   180
TNLVAGCLQL NPRTFLPEQN QDMPPHLPTA SASFPVHPYS YQSPGLPSPP YGTMDSSHVF   240
HVKPPPHAYS AALEPPFFESP LTDCTSPSFD GPLSPPLSIN GNFSFKHEPS AEFEKNYAFT   300
MHYPAATLAG AQSHGSIFSG TAAPRCEIPI DNIMSFDSHS HHERVMSAQL NAIFHD       356

SEQ ID NO: 68                   moltype = AA  length = 498
FEATURE                         Location/Qualifiers
source                          1..498
                                mol_type = protein
                                organism = Homo sapiens
SEQUENCE: 68
MNQSIPVAPT PPRRVRLKPW LVAQVNSCQY PGLQWVNGEK KLFCIPWRHA TRHGPSQDGD    60
NTIFKAWAKE TGKYTEGVDE ADPAKWKANL RCALNKSRDF RLIYDGPRDM PPQPYKIYEV   120
CSNGPAPTDS QPPEDYSFGA GEEEEEEEL QRMLPSLSLT EDVKWPPTLQ PPTLRPPTLQ   180
PPTLQPPVVL GPPAPDPSPL APPPGNPAGF RELLSEVLEP GPLPASLPPA GEQLLPDLLI   240
SPHMLPLTDL EIKFQYRGRP PRALTISNPH GCRLFYSQLE ATQEQVELFG PISLEQVRFP   300
SPEDIPSDKQ RFYTNQLLDV LDRGLILQLQ GQDLYAIRLC QCKVFWSGPC ASAHDSCPNP   360
IQREVKTKLF SLEHFLNELI LFQKGQTNTP PPFEIFFCFG EEWPDRKPRE KKLITVQVVP   420
VAARLLLEMF SGELSWSADS IRLQISNPDL KDRMVEQFKE LHHIWQSQQR LQPVAQAPPG   480
AGLGVGQGPW PMHPAGMQ                                                 498

SEQ ID NO: 69                   moltype = AA  length = 427
FEATURE                         Location/Qualifiers
source                          1..427
                                mol_type = protein
                                organism = Homo sapiens
SEQUENCE: 69
MGTPKPRILP WLVSQLDLGQ LEGVAWVNKS RTRFRIPWKH GLRQDAQQED FGIFQAWAEA    60
TGAYVPGRDK PDLPTWKRNF RSALNRKEGL RLAEDRSKDP HDPHKIYEFV NSGVGDFSQP   120
DTSPDTNGGG STSDTQEDIL DELLGNMVLA PLPDPGPPSL AVAPEPCQP LRSPSLDNPT   180
PFPNLGPSEN PLKRLLVPGE EWEFEVTAFY RGRQVFQQTI SCPEGLRLVG SEVGDRTLPG   240
WPVTLPDPGM SLTDRGVMSY VRHVLSCLGG GLALWRAGQW LWAQRLGHCH TYWAVSEELL   300
PNSGHGPDGE VPKDKEGGVF DLGPFIVDLI TFTEGSGRSP RYALWFCVGE SWPQDQPWTK   360
RLVMVKVVPT CLRALVEMAR VGGASSLENT VDLHISNSHP LSLTSDQYKA YLQDLVEGMD   420
FQGPGES                                                             427

SEQ ID NO: 70                   moltype = AA  length = 750
FEATURE                         Location/Qualifiers
source                          1..750
                                mol_type = protein
                                organism = Homo sapiens
SEQUENCE: 70
MSQWYELQQL DSKFLEQVHQ LYDDSFPMEI RQYLAQWLEK QDWEHAANDV SFATIRFHDL    60
LSQLDDQYSR FSLENNFLLQ HNIRKSKRNL QDNFQEDPIQ MSMIIYSCLK EERKILENAQ   120
RFNQAQSGNI QSTVMLDKQK ELDSKVRNVK DKVMCIEHEI KSLEDLQDEY DFKCKTLQNR   180
EHETNGVAKS DQKQEQLLLK KMYLMLDNKR KEVVHKIIEL LNVTELTQNA LINDELVEWK   240
RRQQSACIGG PPNACLDQLQ NWFTIVAESL QQVRQQLKKL EELELEQKYTYE HDPITKNKQV   300
LWDRTFSLFQ QLIQSSFVVE RQPCMPTHPQ RPLVLKTGVQ FTVKLRLLVK LQELNYNLKV   360
KVLFDKPDVNE RNTVKGFRKF NILGTHTKVM NMEESTNGSL AAEFRHLQLK EQKNAGTRTN   420
EGPLIVTEEL HSLSFETQLC QPGLVIDLET TSLPVVVISN VSQLPSGWAS ILWYNMLVAE   480
PRNLSFFLTP PCARWAQLSE VLSWQFSSVT KRGLNVDQLN MLGEKLLGPN ASPDGLIPWT   540
RFCKENINDK NFPFWLWIES ILELIKKHLL PLWNDGCIMG FISKERERAL LKDQQPGTFL   600
LRFSESSREG AITFTWVERS QNGGEPDFHA VEPYTKKELS AVTFPDIIRN YKVMAAENIP   660
ENPLKYLYPN IDKDHAFGKY YSRPKEAPEP MELDGPKGTG YIKTELISVS EVHPSRLQTT   720
DNLLPMSPEE FDEVSRIVGS VEFDSMMNTV                                    750

SEQ ID NO: 71                   moltype = AA  length = 225
FEATURE                         Location/Qualifiers
source                          1..225
                                mol_type = protein
                                organism = Homo sapiens
SEQUENCE: 71
MVTHSKFPAA GMSRPLDTSL RLKTFSSKSE YQLVVNAVRK LQESGFYWSA VTGGEANLLL    60
SAEPAGTFLI RDSSDQRHFF TLSVKTQSGT KNLRIQCEGG SFSLQSDPRS TQPVPRFDCV   120
LKLVHHYMPP PGAPSFPSPP TEPSSEVPEQ PSAQPLPGSP PRRAYYIYSG GEKIPLVLSR   180
PLSSNVATLQ HLCRKTVNGH LDSYEKVTQL PGPIREFLDQ YDAPL                   225

SEQ ID NO: 72                   moltype = AA  length = 770
FEATURE                         Location/Qualifiers
source                          1..770
                                mol_type = protein
                                organism = Homo sapiens
SEQUENCE: 72
```

```
MAQWNQLQQL DTRYLEQLHQ LYSDSFPMEL RQFLAPWIES QDWAYAASKE SHATLVFHNL    60
LGEIDQQYSR FLQESNVLYQ HNLRRIKQFL QSRYLEKPME IARIVARCLW EESRLLQTAA   120
TAAQQGGQAN HPTAAVVTEK QQMLEQHLQD VRKRVQDLEQ KMKVVENLQD DFDFNYKTLK   180
SQGDMQDLNG NNQSVTRQKM QQLEQMLTAL DQMRRSIVSE LAGLLSAMEY VQKTLTDEEL   240
ADWKRRQQIA CIGGPPNICL DRLENWITSL AESQLQTRQQ IKKLEELQQK VSYKGDPIVQ   300
HRPMLEERIV ELFRNLMKSA FVVERQPCMP MHPDRPLVIK TGVQFTTKVR LLVKFPELNY   360
QLKIKVCIDK DSGDVAALRG SRKFNILGTN TKVMNMEESN NGSLSAEFKH LTLREQRCGN   420
GGRANCDASL IVTEELHLIT FETEVYHQGL KIDLETHSLP VVVISNICQM PNAWASILWY   480
NMLTNNPKNV NFFTKPPIGT WDQVAEVLSW QFSSTTKRGL SIEQLTTLAE KLLGPGVNYS   540
GCQITWAKFC KENMAGKGFS FWVWLDNIID LVKKYILALW NEGYIMGFIS KERERAILST   600
KPPGTFLLRF SESSKEGGVT FTWVEKDISG KTQIQSVEPY TKQQLNNMSF AEIIMGYKIM   660
DATNILVSPL VYLYPDIPKE EAFGKYCRPE SQEHPEADPG SAAPYLKTKF ICVTPTTCSN   720
TIDLPMSPRT LDSLMQFGNN GEGAEPSAGG QFESLTFDME LTSECATSPM             770

SEQ ID NO: 73           moltype = AA  length = 246
FEATURE                 Location/Qualifiers
source                  1..246
                        mol_type = protein
                        organism = Homo sapiens
SEQUENCE: 73
MELVLTQTPS PVSAVVGGTV TINCQSSQSV WGNNRLSWYQ QKPGQPPRLL MYYASNLASG    60
VSSRFKGSGS GTQFTLTISD VQCDDAATYY CQGGFECSGG DCVGFGGGTE LEILGGSSRS   120
SSSGGGGSGG GGQSVEESGG RLVAPGGSLT LTCTVSGIDL SSDAMSWVRQ APGKGLEWIG   180
TIYGSAGTYY ATWAKGRFTI SKTSTTVDLK MTSLTTEDTA TYFCTRAFSN TRLDLWGQGT   240
LVTISS                                                              246

SEQ ID NO: 74           moltype = AA  length = 233
FEATURE                 Location/Qualifiers
source                  1..233
                        mol_type = protein
                        organism = Homo sapiens
SEQUENCE: 74
MSQSNRELVV DFLSYKLSQK GYSWSQFSDV EENRTEAPEG TESEMETPSA INGNPSWHLA    60
DSPAVNGATG HSSSLDAREV IPMAAVKQAL REAGDEFELR YRRAFSDLTS QLHITPGTAY   120
QSFEQVVNEL FRDGVNWGRI VAFFSFGGAL CVESVQKEMQ VLVSRIAAWM ATYLNDHLEP   180
WIQENGGWDT FVELYGNNAA AESRKGQERF NRWFLTGMTV AGVVLLGSLF SRK          233

SEQ ID NO: 75           moltype = AA  length = 312
FEATURE                 Location/Qualifiers
source                  1..312
                        mol_type = protein
                        organism = Homo sapiens
SEQUENCE: 75
MANNDAVLKR LEQKGAEADQ IIEYLKQQVS LLKEKAILQA TLREEKKLRV ENAKLKKEIE    60
ELKQELIQAE IQNGVKQIPF PSGTPLHANS MVSENVIQST AVTTVSSGTK EQIKGGTGDE   120
KKAKEKIEKK GEKKEKKQQS IAGSADSKPI DVSRLDLRIG CIITARKHPD ADSLYVEEVD   180
VGEIAPRTVV SGLVNHVPLE QMQNRMVILL CNLKPAKMRG VLSQAMVMCA SSPEKIEILA   240
PPNGSVPGDR ITFDAFPGEP DKELNPKKKI WEQIQPDLHT NDECVATYKG VPFEVKGKGV   300
CRAQTMSNSG IK                                                       312

SEQ ID NO: 76           moltype = AA  length = 320
FEATURE                 Location/Qualifiers
source                  1..320
                        mol_type = protein
                        organism = Homo sapiens
SEQUENCE: 76
MPMYQVKPYH GGGAPLRVEL PTCMYRLPNV HGRSYGPAPG AGHVQEESNL SLQALESRQD    60
DILKRLYELK AAVDGLSKMI QTPDADLDVT NIIQADEPTT LTTNALDLNS VLGKDYGALK   120
DIVINANPAS PPLSLLVLHR LLCEHFRVLS TVHTHSSVKS VPENLLKCFG EQNKKQPRQD   180
YQLGFTLIWK NVPKTQMKFS IQTMCPIEGE GNIARFLFSL FGQKHNAVNA TLIDSWVDIA   240
IFQLKEGSSK EKAAVFRSMN SALGKSPWLA GNELTVADVV LWSVLQQIGG CSVTVPANVQ   300
RWMRSCENLA PFNTALKLLK                                               320

SEQ ID NO: 77           moltype = AA  length = 233
FEATURE                 Location/Qualifiers
source                  1..233
                        mol_type = protein
                        organism = Homo sapiens
SEQUENCE: 77
MVSKGEEDNM AIIKEFMRFK VHMEGSVNGH EFEIEGEGEG RPYEGTQTAK LKVTKGGPLP    60
FAWDILSPQF MYGSKAYVKH PADIPDYLKL SFPEGFKWER VMNFEDGGVV TVTQDSSLQD   120
GEFIYKVKLR GTNFPSDGPV MQKKTMGWEA SSERMYPEDG ALKGEIKQRL KLKDGGHYDA   180
EVKTTYKAKK PVQLPGAYNV NIKLDITSHN EDYTIVEQYE RAEGRHSTGG MDE          233

SEQ ID NO: 78           moltype = AA  length = 267
FEATURE                 Location/Qualifiers
source                  1..267
                        mol_type = protein
                        organism = Homo sapiens
```

-continued

```
SEQUENCE: 78
MVSKGEELFT GVVPILVELD GDVNGHKFSV SGEGEGDATY GKLTLKFICT TGKLPVPWPT    60
LVTTLTYGVQ CFSRYPDHMK QHDFFKSAMP EGYVQERTIF FKDDGNYKTR AEVKFEGDTL   120
VNRIELKGID FKEDGNILGH KLEYNYNSHN VYIMADKQKN GIKVNFKIRH NIEDGSVQLA   180
DHYQQNTPIG DGPVLLPDNH YLSTQSALSK DPNEKRDHMV LLEFVTAAGI TLGMDELYKG   240
SGSGLRSRAQ ASNSAVDGTA GPGSTGS                                      267

SEQ ID NO: 79           moltype = AA  length = 425
FEATURE                 Location/Qualifiers
source                  1..425
                        mol_type = protein
                        organism = Homo sapiens
SEQUENCE: 79
MADKEAAFDD AVEERVINEE YKIWKKNTPF LYDLVMTHAL EWPSLTAQWL PDVTRPEGKD    60
FSIHRLVLGT HTSDEQNHLV IASVQLPNDD AQFDASHYDS EKGEFGGFGS VSGKIEIEIK   120
INHEGEVNRA RYMPQNPCII ATKTPSSDVL VFDYTKHPSK PDPSGECNPD LRLRGHQKEG   180
YGLSWNPNLS GHLLSASDDH TICLWDISAV PKEGKVVDAK TIFTGHTAVV EDVSWHLLHE   240
SLFGSVADDQ KLMIWDTRSN NTSKPSHSVD AHTAEVNCLS FNPYSEFILA TGSADKTVAL   300
WDLRNLKLKL HSFESHKDEI FQVQWSPHNE TILASSGTDR RLNVWDLSKI GEEQSPEDAE   360
DGPPELLFIH GGHTAKISDF SWNPNEPWVI CSVSEDNIMQ VWQMAENIYN DEDPEGSVDP   420
EGQGS                                                              425

SEQ ID NO: 80           moltype = AA  length = 375
FEATURE                 Location/Qualifiers
source                  1..375
                        mol_type = protein
                        organism = Homo sapiens
SEQUENCE: 80
MADHSFSDGV PSDSVEAAKN ASNTEKLTDQ VMQNPRVLAA LQERLDNVPH TPSSYIETLP    60
KAVKRRINAL KQLQVRCAHI EAKFYEEVHD LERKYAALYQ PLFDKRREFI TGDVEPTDAE   120
SEWHSENEEE EKLAGDMKSK VVVTEKAAAT AEEPDPKGIP EFWFTIFRNV DMLSELVQEY   180
DEPILKHLQD IKVKFSDPGQ PMSFVLEFHF EPNDYFTNSV LTKTYKMKSE PDKADPFSFE   240
GPEIVDCDGC TIDWKKGKNV TVKTIKKKQK HKGRGTVRTI TKQVPNESFF NFFNPLKASG   300
DGESLDEDSE FTLASDFEIG HFFRERIVPR AVLYFTGEAI EDDDNFEEGE EGEEEELEGD   360
EEGEDEDDAE INPKV                                                   375

SEQ ID NO: 81           moltype = AA  length = 1132
FEATURE                 Location/Qualifiers
source                  1..1132
                        mol_type = protein
                        organism = Homo sapiens
SEQUENCE: 81
MPRAPRCRAV RSLLRSHYRE VLPLATFVRR LGPQGWRLVQ RGDPAAFRAL VAQCLVCVPW    60
DARPPPAAPS FRQVSCLKEL VARVLQRLCE RGAKNVLAFG FALLDGARGG PPEAFTTSVR   120
SYLPNTVTDA LRGSGAWGLL LRRVGDDVLV HLLARCALFV LVAPSCAYQV CGPPLYQLGA   180
ATQARPPPHA SGPRRRLGCE RAWNHSVREA GVPLGLPAPG ARRGGSASR  SLPLPKRPRR   240
GAAPEPERTP VGQGSWAHPG RTRGPSDRGF CVVSPARPAE EATSLEGALS GTRHSHPSVG   300
RQHHAGPPST SRPPRPWDTP CPPVYAETKH FLYSSGDKEQ LRPSFLLSSL RPSLTGARRL   360
VETIFLGSRP WMPGTPRRLP RLPQRYWQMR PLFLELLGNH AQCPYGVLLK THCPLRAAVT   420
PAAGVCAREK PQGSVAAPEE EDTDPRRLVQ LLRQHSSPWQ VYGFVRACLR RLVPPGLWGS   480
RHNERRFLRN TKKFISLGKH AKLSLQELTW KMSVRDCAWL RRSPGVGCVP AAEHRLREEI   540
LAKFLHWLMS VYVVELLRSF FYVTETTFQK NRLFFYRKSV WSKLQSIGIR QHLKRVQLRE   600
LSEAEVRQHR EARPALLTSR LRFIPKPDGL RPIVNMDYVV GARTFRREKR AERLTSRVKA   660
LFSVLNYERA RRPGLLGASV LGLDDIHRAW RTFVLRVRAQ DPPPELYFVK VDVTGAYDTI   720
PQDRLTEVIA SIIKPQNTYC VRRYAVVQKA AHGHVRKAFK SHVSTLTDLQ PYMRQFVAHL   780
QETSPLRDAV VIEQSSSLNE ASSGLFDVFL RFMCHHAVRI RGKSYVQCQG IPQGSILSTL   840
LCSLCYGDME NKLFAGIRRD GLLLRLVDDF LLVTPHLTHA KTFLRTLVRG VPEYGCVVNL   900
RKTVVNFPVE DEALGGTAFV QMPAHGLFPW CGLLLDTRTL EVQSDYSSYA RTSIRASLTF   960
NRGFKAGRNM RRKLFGVLRL KCHSLFLDLQ VNSLQTVCTN IYKILLLQAY RPHACVLQLP  1020
FHQQVWKNPT FFLRVISDTA SLCYSILKAK NAGMSLGAKG AAGPLPSEAV QWLCHQAFLL  1080
KLTRHRVTYV PLLGSLRTAQ TQLSRKLPGT TLTALEAAAN PALPSDFKTI LD          1132

SEQ ID NO: 82           moltype = AA  length = 462
FEATURE                 Location/Qualifiers
source                  1..462
                        mol_type = protein
                        organism = Homo sapiens
SEQUENCE: 82
METEQPEETF PNTETNGEFG KRPAEDMEEE QAFKRSRNTD EMVELRILLQ SKNAGAVIGK    60
GGKNIKALRT DYNASVSVPD SSGPERILSI SADIETIGEI LKKIIPTLEE GLQLPSPTAT   120
SQLPLESDAV ECLNYQHYKG SDFDCELRLL IHQSLAGGII GVKGAKIKEL RENTQTTIKL   180
FQECCPHSTD RVVLIGGKPD RVVECIKIIL DLISESPIKG RAQPYDPNFY DETYDYGGFT   240
MMFDDRRGRP VGFPMRGRGG FDRMPPGRGG RPMPPSRRDY DDMSPRRGRP PPPPGRGGRG   300
GSRARNLPLP PPPPPRGGDL MAYDRRGRPG DRYDGMVGFS ADETWDSAID TWSPSEWQMA   360
YEPQGGSGYD YSYAGGRGSY GDLGGPIITT QVTIPKDLAG SIIGKGGQRI KQIRHESGAS   420
IKIDEPLEGS EDRIITITGT QDQIQNAQYL LQNSVKQYSG KF                     462

SEQ ID NO: 83           moltype = AA  length = 745
FEATURE                 Location/Qualifiers
```

```
source                  1..745
                        mol_type = protein
                        organism = Homo sapiens
SEQUENCE: 83
MERPPGLRPG AGGPWEMRER LGTGGFGNVC LYQHRELDLK IAIKSCRLEL STKNRERWCH    60
EIQIMKKLNH ANVVKACDVP EELNILIHDV PLLAMEYCSG GDLRKLLNKP ENCCGLKESQ   120
ILSLLSDIGS GIRYLHENKI IHRDLKPENI VLQDVGGKII HKIIDLGYAK DVDQGSLCTS   180
FVGTLQYLAP ELFENKPYTA TVDYWSFGTM VFECIAGYRP FLHHLQPFTW HEKIKKKDPK   240
CIFACEEMSG EVRFSSHLPQ PNSLCSLVVE PMENWLQLML NWDPQQRGGP VDLTLKQPRC   300
FVLMDHILNL KIVHILNMTS AKIISFLLPP DESLHSLQSR IERETGINTG SQELLSETGI   360
SLDPRKPASQ CVLDGVRGCD SYMVYLFDKS KTVYEGPFAS RSLSDCVNYI VQDSKIQLPI   420
IQLRKVWAEA VHYVSGLKED YSRLFQGQRA AMLSLLRYNA NLTKMKNTLI SASQQLKAKL   480
EFFHKSIQLD LERYSEQMTY GISSEKMLKA WKEMEEKAIH YAEVGVIGYL EDQIMSLHAE   540
IMELQKSPYG RRQGDLMESL EQRAIDLYKQ LKHRPSDHSY SDSTEMVKII VHTVQSQDRV   600
LKELFGHLSK LLGCKQKIID LLPKVEVALS NIKEADNTVM FMQGKRQKEI WHLLKIACTQ   660
SSARSLVGSS LEGAVTPQTS AWLPPTSAEH DHSLSCVVTP QDGETSAQMI EENLNCLGHL   720
STIIHEANEE QGNSMMNLDW SWLTE                                        745

SEQ ID NO: 84           moltype = AA  length = 968
FEATURE                 Location/Qualifiers
source                  1..968
                        mol_type = protein
                        organism = Homo sapiens
SEQUENCE: 84
MAEDDPYLGR PEQMFHLDPS LTHTIFNPEV FQPQMALPTD GPYLQILEQP KQRGFRFRYV    60
CEGPSHGGLP GASSEKNKKS YPQVKICNYV GPAKVIVQLV TNGKNIHLHA HSLVGKHCED   120
GICTVTAGPK DMVVGFANLG ILHVTKKKVF ETLEARMTEA CIRGYNPGLL VHPDLAYLQA   180
EGGGDRQLGD REKELIRQAA LQQTKEMDLS VVRLMFTAFL PDSTGSFTRR LEPVVSDAIY   240
DSKAPNASNL KIVRMDRTAG CVTGGEEIYL LCDKVQKDDI QIRFYEEEEN GGVWEGFGDF   300
SPTDVHRQFA IVFKTPKYKD INITKPASVF VQLRRKSDLE TSEPKPFLYY PEIKDKEEVQ   360
RKRQKLMPNF SDSFGGGSGA GAGGGGMFGS GGGGGGTGST GPGYSFPHYG FPTYGGITFH   420
PGTTKSNAGM KHGTMDTESK KDPEGCDKSD DKNTVNLFGK VIETTEQDQE PSEATVGNGE   480
VTLTYATGTK EESAGVQDNL FLEKAMQLAK RHANALFDYA VTGDVKMLLA VQRHLTAVQD   540
ENGDSVLHLA IIHLHSQLVR DLLEVTSGLI SDDIINMRND LYQTPLHLAV ITKQEDVVED   600
LLRAGADLSL LDRLGNSVLH LAAKEGHDKV LSILLKHKKA ALLLDHPNGD GLNAIHLAMM   660
SNSLPCLLLL VAAGADVNAQ EQKSGRTALH LAVEHDNISL AGCLLLEGDA HVDSTTYDGT   720
TPLHIAAGRG STRLAALLKA AGADPLVENF EPLYDLDDSW ENAGEDEGVV PGTTPLDMAT   780
SWQVFDILNG KPYEPEFTSD DLLAQGDMKQ LAEDVKLQLY KLEIPDPDK NWATLAQKLG    840
LGILNNAFRL SPAPSKTLMD NYEVSGGTVR ELVEALRQMG YTEAIEVIQA ASSPVKTTSQ   900
AHSLPLSPAS TRQQIDELRD SDSVCDSGVE TSFRKLSFTE SLTSGASLLT LNKMPHDYGQ   960
EGPLEGKI                                                           968
```

The invention claimed is:

1. An exosome comprising
   a transmembrane protein, and
   a target peptide inserted into an extracellular domain of the transmembrane protein.

2. The exosome of claim 1, wherein the transmembrane protein comprises tetraspanin.

3. The exosome of claim 2, wherein the tetraspanin comprises CD9.

4. The exosome of claim 3, wherein said CD9 has an amino acid sequence of SEQ ID NO: 3.

5. The exosome of claim 3, wherein the target peptide is inserted between the amino acids corresponding to amino acid positions 170 and 171 from the N-terminus of CD9.

6. The exosome of claim 1, wherein the target peptide is a peptide capable of transferring the exosome to a specific tissue.

7. The exosome of claim 6, wherein the specific tissue is selected from the group comprising blood brain barrier, inflamed blood vessels, striated muscle, liver, and cancer tissue.

8. The exosome of claim 1, wherein the target peptide is selected from the group consisting of angiopep-2, ApoB, ApoE, VCAM-1 (vascular cell adhesion molecule-1) internalization sequence peptide complex, striated muscle target peptide, Peptide-22, THR, THR retro-enantio, CRT, Leptin30, RVG (Rabies Virus Glycoprotein) 29, CDX, Apamin, MiniAp-4, GSH, G23, g7, TGN, TAT (45-57), SynB1, Diketopiperazines and PhPro.

9. The exosome of claim 1, wherein the target peptide is inserted into the extracellular membrane domain of the transmembrane protein at a location that does not affect the expression or the function of the transmembrane.

10. A pharmaceutical composition comprising an exosome prepared of claim 1.

11. A method of producing the exosome of claim 1, comprising:
   a) preparing an expression vector by inserting a target peptide into an extracellular domain of the transmembrane protein; and
   b) introducing the expression vector of the step a) into an exosome-producing cell; and
   c) producing the exosome, wherein the target peptide is expressed on the surface of the exosome.

12. The method of claim 11, wherein the transmembrane protein comprises tetraspanin.

13. The method of claim 12, wherein the tetrapanin comprises CD9.

14. The method of claim 13, wherein said CD9 has an amino acid sequence of SEQ ID NO: 3.

15. The method of claim 13, wherein the target peptide is inserted between the amino acids corresponding to amino acid positions 170 and 171 from the N-terminus of CD9.

16. The method of claim 11, wherein the exosome-producing cell is selected from the group consisting of B-lymphocytes, T-lymphocytes, dendritic cells, macrophage cells, macrophages, stem cells, HEK293T cells, and tumor cells.

* * * * *